US008268493B2

(12) United States Patent
Cetegen et al.

(10) Patent No.: US 8,268,493 B2
(45) Date of Patent: Sep. 18, 2012

(54) FIBER OPTIC BASED IN-SITU DIAGNOSTICS FOR PEM FUEL CELLS

(75) Inventors: Baki M. Cetegen, Glastonbury, CT (US); Michael W. Renfro, Storrs, CT (US); Saptarshi Basu, Storrs, CT (US)

(73) Assignee: University of Connecticut, Farmington, CT (US)

( * ) Notice: Subject to any disclaimer, the term of this patent is extended or adjusted under 35 U.S.C. 154(b) by 1321 days.

(21) Appl. No.: 11/807,880

(22) Filed: May 30, 2007

(65) Prior Publication Data
US 2008/0118783 A1 May 22, 2008

Related U.S. Application Data

(60) Provisional application No. 60/809,422, filed on May 30, 2006.

(51) Int. Cl.
 *H01M 8/06* (2006.01)
 *H01M 8/00* (2006.01)
 *H01M 8/04* (2006.01)

(52) U.S. Cl. ........ 429/427; 429/400; 429/428; 429/433; 429/442; 429/443

(58) Field of Classification Search ............ None
See application file for complete search history.

(56) References Cited

U.S. PATENT DOCUMENTS

2005/0069746 A1* 3/2005 Kabasawa ............... 429/34
2008/0003473 A1* 1/2008 Tung et al. ............... 429/26

OTHER PUBLICATIONS

Cetegen et al., In Situ Diagnostics for Measurements of Water Vapor Partial Pressure in a PEM Fuel Cell, Feb. 2006, Journal of Fuel Cell Science and Technology, vol. 3, pp. 1-7.*
B.H. Armstrong, Spectrum Line Profiles: The Voigt Function, J. Quant. Spectrosc. Radiat. Transfer, vol. 7, pp. 61-88, (1966).
M.L. Perry, et al., Mass Transport in Gas-Diffusion Electrodes: A Diagnostic Tool for Fuel-Cell Cathodes, J. Electrochem. Soc., vol. 145, No. 1, pp. 5-15 (1998).
J. Stumper, et al., In-situ Methods for the Determination of Current Distributions in PEM Fuel Cells, Electrochem. Acta, vol. 43, No. 24, pp. 3773-3783, (1998).
J.T. Mueller, et al., Characterization of Direct Methanol Fuel Cells by AC Impedance, Journal of Power Sources, vol. 75, pp, 139-143 (1998).

(Continued)

*Primary Examiner* — Barbara Gilliam
*Assistant Examiner* — Adam A Arciero
(74) *Attorney, Agent, or Firm* — McCarter & English, LLP

(57) ABSTRACT

The present disclosure relates to in-situ, line-of-sight measurements of partial pressure and temperature associated with at least one flow channel of a fuel cell. Tunable diode laser absorption spectroscopy (TDLAS) is employed for measurements for which water transition states sensitive to temperature and partial pressure are utilized. Measurements are achievable for a fuel cell operating under both steady-state and time-varying load conditions. For steady-state operation, the water partial pressure increases with increasing current density on a cathode side of the fuel cell due to production of water by electrochemical reaction. Temperature in a gas phase remains relatively constant since the fuel cell housing temperature is controlled externally. For non-steady-state operation of the fuel cell through a time-varying current profile, the water partial pressure responds to the load changes rapidly and follows a current profile. The gas temperature varies in response to the dynamic loading and departures from steady-state conditions become more apparent at higher fuel cell operating temperatures.

20 Claims, 14 Drawing Sheets

OTHER PUBLICATIONS

L.S. Rothman, et al., J. Quant. Spectrosc. Radiat. Transfer, vol. 60, No. 5, pp. 665-710 (1998).

G. Alberti, et al., Journal of Membrane Science, vol. 185, pp. 73-81 (2001).

A.E. Russell, et al., In situ X-ray Absorption Spectroscopy and X-Ray Diffraction of Fuel Cell Electrocatalysts, Journal of Power Sources, vol. 96, pp. 226-232 (2001).

P. Costamagna, et al., Quantum Jumps in the PEMFC Science and Technology From the 1960's to the Year 2000, Journal of Power Sources, vol. 102, pp. 253-269 (2001).

R. Viswanathan, et al., In Situ X-Ray Absorption Fuel Cell, Review of Scientific Instruments, vol. 73, pp. 2124-2127 (2002).

M.M. Mench, et al., In Situ Current Distributioin Measurements in Polymer Electrolyte Fuel Cells, Journal of the Electrochemical Society, vol. 150, No. 8, pp. A1052-A1059 (2003).

M.M. Mench, et al., In Situ Water Distribution Measurements in a Polmer Electrolyte Fuel Cell, Journal of Power Sources, vol. 124, pp. 90-98 (2003).

R. Satija, et al., In Situ Neutron Imaging Technique for Evaluation of Water Management Systems in Operating PEM Fuel Cells, Journal of Power Sources, vol. 129, pp. 238-245 (2004).

I. Tkach, et al., In Situ Study of Methanol Oxidation on Pt and Pt/Ru-Mixed with Nafion Anodes in a Direct Methanol Fuel Cell by Means of FTIR Spectroscopy, Phys. Chem. Chem. Phys., vol. 6, pp. 5419-5426 (2004).

V.R. Albertini, et al., In Situ XRD Studies of the Hydration Degree of the Polymeric Membrane in a Fuel Cell, Electrochemical and Solid-State Letters, vol. 7, No. 12, pp. A519-A521 (2005).

F. Barbir, et al., Relationship Between Pressure Drop and Cell Resistance as a Diagnostic Tool for PEM Fuel Cells, Journal of Power Sources, vol. 141, pp. 96-101 (2005) ; and W.S. He, G.Y. Lin, T. Van Nguyen, AIChE J., 49 (2003) 3221-3228.

D. Kramer, et al., In Situ Diagnostic of Two-Phase Flow Phenomena in Polymer Electrolyte Fuel Cells by Neutron Imaging: Part A. Experimental, Data Treatment and Quantification, Electrochemica Acta, vol. 50, pp. 2603-2614 (2005).

Y.P. Patil, et al., In-Situ pH Measurement in a Nafion Based Polymer Electrolyte Fuel Cell by Fluorescence Spectroscopy, Prepr. Pap.-Am. Chem. Soc., Div. Fuel Chem., vol. 49, pp. 683-684 (2004).

H. Yang, et al., In Situ Visualization Study of $CO_2$ Gas Bubble Behavior in DMFC Anode Flow Fields, Journal of Power Sources, vol. 139, pp. 79-90 (2005).

Y.P. Patil, et al., In Situ Water Sensing in a Nafion Membrane by Fluorescence Spectroscopy, Ind. Eng. Chem. Res., vol. 44, pp. 6141-6147 (2005).

Q. Dong, et al., Real-Time Water Distribution in a Polymer Electrolyte Fuel Cell, Journal of Power Sources, vol. 139, pp. 106-114 (2005).

J. Stumper, et al., In Situ Determination of MEA Resistance and Electrode Diffusivity of a Fuel Cell, Journal of the Electrochemical Society, vol. 152, pp. A837-A844 (2005).

US Fuel Cell Council, Protocol on Fuel Cell Component Testing, Document No. USFCC 04-003, pp. cover and 1-21, www.usfcc.com.

S.S. Penner, Quantitative Molecular Spectroscopy and Gas Emissivities, Chapter 1: Thermal Radiation, pp. 1-15, Addison-Wesley,1959.

J. Larminie, et al., Fuel Cell Systems Explained, Chapter 1: Introduction: Hydrogen Fuel Cells—Basic Principles, Wiley, New York, 2000, pp. 1-6 and pp. 69-77.

\* cited by examiner

FIBER OPTIC BASED IN-SITU DIAGNOSTICS FOR PEM FUEL CELLS

CROSS-REFERENCE TO RELATED APPLICATIONS

The present application claims the benefit under 35 U.S.C. §119(e) of U.S. Provisional Application No. 60/809,422, filed May 30, 2006. The foregoing application is also hereby incorporated by reference in its entirety for all purposes.

BACKGROUND

1. Technical Field

The present disclosure relates to systems and methods for optical diagnostics in a Proton Exchange Membrane (PEM) fuel cell using absorption spectroscopy.

2. Background Art

Proton exchange membrane (PEM) fuel cells generate electricity directly through two electrochemical reactions. These reactions take place at the interface between a proton conductive membrane and catalyst electrodes. In a PEM fuel cell, controlled hydration of the membrane is required to ensure effective operation. The hydrogen and oxygen feed streams are typically hydrated to bring water vapor into the cell. Several transport processes are responsible for non-homogeneous distribution of water across the cell cross-section including diffusion due to partial pressure gradients and electro-osmotic drag of water by protons through the membrane (see, e.g., J. Larminie, A. Dicks, *Fuel Cell Systems Explained*, Wiley, New York, 2000, pp. 1-6 and pp. 69-77; and P. Costamagna, S. Sirinivasan, *J. Power Sources*, 102 (2001) 253-269). In addition, the cathode reactions also produce water that may condense depending on local temperature and partial pressure with respect to the fuel cell.

Overall performance of the fuel cell can be very sensitive to water management since excessive water can lead to flooding and limit the rate of reactant transport to the electrodes. Moreover, a reduction in water can decrease the protonic conductivity of the membrane. Nafion©, which is currently the most common membrane material exhibits a protonic conductivity change of an order of magnitude due to variation of relative humidity between 35 and 85% (see, e.g., G. Alberti, M. Casciola, L. Massinelli, B. Bauer, *J. of Membrane Sci.*, 185 (2001) 73-81). Similarly, the temperature of a PEM fuel cell impacts performance of the catalyst electrodes, water transport and liquid/vapor balance.

Understanding of the distribution of water and local temperatures within operating fuel cells can significantly impact optimization of fuel cell system operation and design. Accurate, fast, in-situ measurements of water concentration would enable both better understanding of water transport, thereby improving cell design and advanced control strategies.

Development of tools for sensing temperature and chemical species in fuel cells is a relatively new area of research. Until recently, most measurements in fuel cell systems were limited to global measurements of electrical cell performance. Polarization curve measurements, for example, are routinely used to track cell performance and can be combined with simple models to diagnose component problems in the cell (see, e.g., M. L. Perry, J Newman, E. J. Cairns, *J. Electrochem. Soc.*, 145 (1998) 5-15). More recent refinement of global measurement techniques has permitted monitoring of flooding or drying conditions based on pressure drop across the cell (see, e.g., F. Barbir, H. Gorgun, X. Wang, *J. Power Sources*, 141 (2005) 96-101; and W. S. He, G. Y. Lin, T. Van Nguyen, *AIChE J.*, 49 (2003) 3221-3228), separation of anode and cathode contributions to cell polarization based on impedance spectroscopy (see, e.g., J. T. Mueller, P. M. Urban, *J. Power Sources*, 75 (1998) 139-143), and diagnosis of gas diffusivities at electrodes based on rapid gas supply interruption (see, e.g., J. Stumper, H. Haas, A. Granados, *J. Electrochem. Soc.*, 152 (2005) A837-A844). However, these techniques are generally limited to providing only information integrated across the cell.

More recent developments have enabled characterization of local cell conditions. The development of segmented fuel cells enables measurements of local electrical performance (see, e.g., J. Stumper, S. A. Campbell, D. P. Wilkinson, M. C. Johnson, M. Davis, *Electrochem. Acta*, 43 (1998) 3773-3783; and M. M. Mench, C. Y. Wang, M Ishikawa, *J. Electrochem. Soc.*, 150 (2003) A1052-A1059). Observation of local chemical conditions have been made using simple visual observations of bubble formation through windowed direct methanol fuel cells (see, e.g., H. Yang, T. S. Zhao, Q. Ye, *J. Power Sources*, 139 (2005) 79-90), physical probe measurements using gas chromatography (see, e.g., Q. Dong, J. Kull, M. M. Mench, *J. Power Sources*, 139 (2005) 106-114; and M. M. Mench, Q. L. Dong, C. Y. Wang, *J. Power Sources*, 124 (2003) 90-98), and more sophisticated optical approaches such as liquid water measurements via neutron scattering (see, e.g., D. Kramer, J. Zhang, R. Shimoi, E. Lehmann, A. Wokaun, K. Shinohara, G. G. Scherer, *Electrochem. Acta*, 50 (2005) 2603-2614; and R. Satija, D. L. Jacobson, M. Arif, S. A. Werner, *J. Power Sources*, 129 (2004) 238-245), membrane hydration via x-ray scattering (see, e.g., V. R. Albertini, B. Paci, A. Generosi, S. Panero, M. A. Navarra, M. di Michiel, *Electrochem. Sol. State Let.*, 7 (2005) A519-A521), catalyst composition via x-ray absorption (see, e.g., R. Viswanathan, R. Liu, E. S. Smotkin, *Rev. Sci. Instrum.*, 73 (2002) 2124-2127; and A. E. Russell, S. Maniguet, R. J. Mathew, J. Yao, M. A. Roberts, D. Thompsett, *J. Power Sources*, 96 (2001) 226-232), Fourier transform infrared (FTIR) spectroscopy (see e.g., I. Tkach, A. Panchenko, T. Kaz, V. Gogel, K. A. Friedrich, E. Roduner, *Phys. Chem. Chem. Phys.*, 6 (2004) 5419-5426), and membrane water content and acidity via fiber based fluorescence (see, e.g., Y. P. Patil, T. A. P. Seery, M. T. Shaw, R. S. Parnas, *ACS Fuel Chem. Pre.*, 49 (2004) 683; and Y. P. Patil, T. A. P. Seery, M. T. Shaw, R. S. Parnas, *Ind. Eng. Chem. Res.*, 44 (2005) 6141).

Most of the techniques available for local measurements of chemical composition are limited by either requiring extractive sampling as in the case of gas chromatography and FTIR spectroscopy, which limits their temporal response, or by using facilities that are not easily implemented in routine system measurements, as in the case of neutron scattering and x-ray absorption. Transient gas-phase measurements using non-intrusive laser-based in-situ diagnostics during a dynamic cycle of fuel cell operation currently do not exist.

Existing water vapor partial pressure measurements related to fuel cell operation are confined to probe sample extraction and inlet and outlet measurements using gas chromatography and Fourier transform infrared spectroscopy. These measurements provide only integrated values across a fuel cell and do not provide local measurements. Accordingly, a need exists for systems and methods for convenient and in-situ gas phase concentration measurement of an operating fuel cell, particularly related to PEM fuel cells.

These and other disadvantages and/or limitations are addressed and/or overcome by the systems and methods of the present disclosure.

SUMMARY

The present disclosure relates to systems and methods for measuring partial pressure and temperature within a fuel cell.

In an exemplary embodiment, the system includes: (a) a fuel cell having a proton exchange membrane (PEM)-electrode assembly and a bipolar plate that includes at least one flow channel adapted to allow for transmission of light through the at least one flow channel; (b) at least one light source adapted to transmit light through the at least one flow channel; (c) at least one reference light sensor for measuring the light transmitted from the light source prior to passing through the at least first flow channel; and (d) at least one transmission light sensor for measuring the light transmitted through the at least one flow channel. The measured light transmitted through the at least one flow channel represents light absorption through the flow channel and is processed along with the reference light measurement to determine values for at least one of a gas species partial pressure or a fuel cell temperature.

In an exemplary embodiment, the at least one flow channel associated with the bipolar plate includes oppositely positioned first and second collimating lenses coupled with optical fibers. Each collimating lens is positioned at opposite ends of the flow channel. The optical fibers are selected with reference to a specific wavelength associated with the light source and with reference to an absorption profile of a gas species. In an exemplary embodiment, the light source is a laser light source and the transmitted light is a laser beam. In a further exemplary embodiment, the bipolar plate includes at least one flow channel adapted to allow for transmission of a near infrared laser beam through the flow channel. The gas species can be a gas selected from the group consisting of water vapor, CO, $CO_2$, $CH_4$, $H_2$, $O_2$, and combinations thereof.

In an exemplary embodiment, the measured light transmission is characterized by tunable diode laser absorption spectroscopy (TDLAS). The light measurements can be taken during steady-state fuel cell operation and/or during dynamic fuel cell operation. Typically, the reference light sensor and the transmission light sensor are photodiode sensors characterized by a fiber optic coupled diode-sensor. The transmitted light is characterized by a light wavelength transmitted over several water rotational and vibrational transition states in the fuel cell.

In an exemplary embodiment, the bipolar plate includes a plurality of flow channels. Each of the plurality of flow channels is adapted to allow for light to pass through the flow channel and be measured by a light sensor. Light measurements can be taken in a non-operating fuel cell having input gas streams of known humidity thereby allowing for calibration of fuel cell parameters. The parameters are selected from the group consisting of light absorption, gas inputs to the fuel cell, operating temperature, humidity of gas inputs and combinations thereof. In an exemplary embodiment, light measurements are taken in a non-operating fuel cell having gas streams of known humidity thereby allowing for testing of fuel cell response to different fuel cell parameters. In a further exemplary embodiment, the light measurements are taken during fuel cell operation to allow for examining effects of incoming gas humidity and load on water vapor partial pressure in the at least one flow channel.

In an exemplary embodiment, the partial pressure and temperature values resulting from measured light transmission are received by at least one fuel cell controller adapted to process the measured light values and, based on the measurements, control output of at least one system component selected from the group consisting of a heating source adapted to heat the fuel cell, at least one humidifier adapted to humidify at least one inlet stream into the fuel cell, a load box or external circuit adapted to apply load on the fuel cell, and combinations thereof to operate the fuel cell at desired operating conditions.

In an exemplary embodiment, the partial pressure values resulting from measured light transmission and the reference light transmission sensor are received by at least one data acquisition and laser controller adapted to process the measured values and, based on the measurements, control output of at least one system component selected from the group consisting of a light source temperature controller, a light source current controller and combinations thereof to transmit light at a desired wavelength.

The present disclosure provides for several measurements to be taken across the at least one flow channel to generate at least one parameter profile for at least one known parameter versus the partial pressure and temperature measurements. In an exemplary embodiment, the collimating lenses are adapted to: (i) seal the flow channel; and (ii) collimate the transmitted light.

The present disclosure provides for a system for measuring parameters associated with a fuel cell in situ including: (a) a fuel cell including: (i) an air stream inlet on a cathode side; (ii) a hydrogen stream inlet on an anode side; and (iii) a bipolar plate positioned between the cathode side and the anode side, the bipolar plate having at least one flow channel adapted to allow for light transmission through the flow channel; (b) a light source adapted to transmit a light beam through the at least one flow channel; (c) a reference light sensor coupled to the light transmission prior to transmission of light through the flow channel; (d) a transmission light sensor coupled to the light transmitted through the flow channel; and (e) a data acquisition and light control apparatus coupled to the reference light sensor, the transmission light sensor, a light source temperature controller and a light source current controller. Typically, the light source temperature controller and the light source current controller are in communication with the light source and are operably adapted to modify the light transmission from the light source. In an exemplary embodiment, the data acquisition and light control apparatus is a computer that processes the reference light values and the transmitted light values from the light sensors to generate data on gas species partial pressure and fuel cell operating temperature.

In an exemplary embodiment according to the present disclosure, the system further includes: (i) a hydrogen stream humidifier adapted to humidify an inlet hydrogen stream coupled to the hydrogen stream inlet associated with the fuel cell; (ii) an air stream humidifier adapted to humidify an inlet air stream coupled to the air stream inlet associated with the fuel cell; and (iii) a heating source coupled to the fuel cell. The hydrogen stream humidifier, the air stream humidifier and the heating source can each be in communication with a fuel cell controller adapted to adjust: (i) the humidity of the inlet hydrogen stream, (ii) the humidity of the inlet air stream and (iii) the temperature of the fuel cell. In an exemplary embodiment, the fuel cell controller is in communication with an electrical load box coupled to the fuel cell. The electrical load box is adapted to deliver voltage to the fuel cell.

In an exemplary embodiment, the light source is a laser light source adapted to transmit a laser beam. In a further exemplary embodiment, the system further includes an optical splitter adapted to split the light transmitted from the light source into a reference beam coupled to the reference light sensor and a transmission beam that passes through the at least one flow channel coupled to the transmission light sensor. Typically, the light sensors are photodiode light sensors.

The present disclosure provides for an exemplary method for measuring partial pressure and temperature of a fuel cell, including the steps of: (a) transmitting light from a light source through at least a first flow channel of a bipolar plate included in a fuel cell; (b) measuring the transmitted light from the light source by a reference light sensor; (c) measuring the transmitted light through the flow channel by at least one transmission light sensor coupled to the flow channel, and (d) generating at least one of gas species partial pressure data or fuel cell temperature data from the light measured by the reference light sensor and the transmission light sensor. In an exemplary embodiment the reference light sensor and the transmission light sensor are in communication with a data acquisition and light controller apparatus adapted to receive the sensor measurements and generate the partial pressure and temperature data. The data acquisition and light controller apparatus can further be in communication with a light source temperature controller and a light source current controller coupled to the light source.

In an exemplary embodiment, the light source is a laser light source adapted to transmit laser light beams through the flow channel. The fuel cell typically includes a hydrogen stream inlet and an air stream inlet. Generally, the hydrogen stream inlet passes through a hydrogen stream humidifier and the air stream inlet passes through an air stream humidifier. In an exemplary embodiment, the hydrogen stream humidifier and the air stream humidifier are in communication with a fuel cell controller.

The present disclosure provides for an exemplary method such that the fuel cell is coupled to an electrical load box adapted to deliver voltage to the fuel cell and a heating source adapted to heat the fuel cell. The electrical load box and the heating source are in communication with the fuel cell controller.

Additional features, functions and benefits of the disclosed systems and methods will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein.

DESCRIPTION OF EXEMPLARY EMBODIMENT(S)

Figure 1:
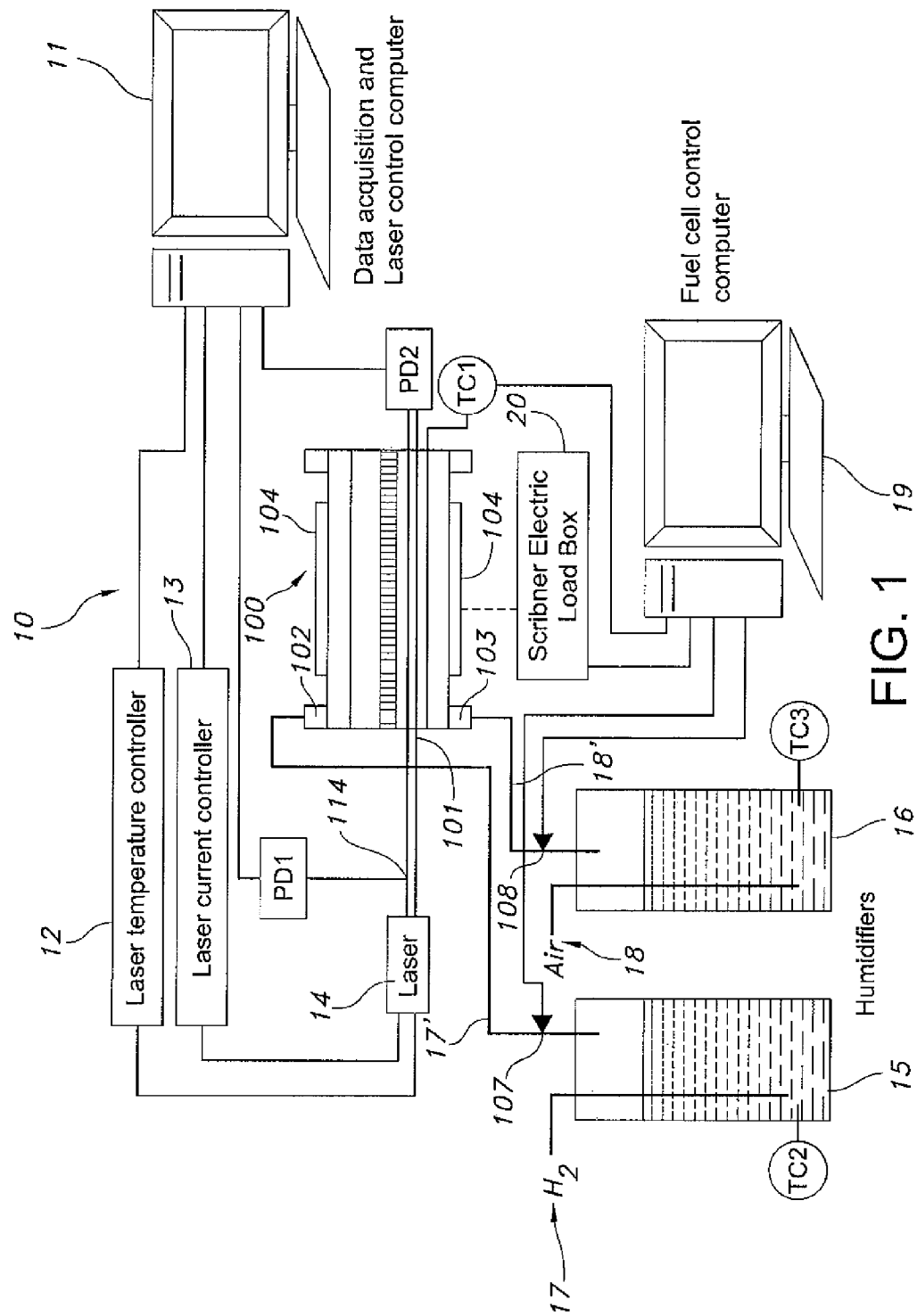
FIG. 1 is a schematic illustrating an experimental setup for calibration, steady-state, and dynamic testing of a fuel cell system associated with the present disclosure.

In an exemplary embodiment, the present disclosure provides for systems and methods for measuring gas partial pressure and temperature of a fuel cell in-situ utilizing tunable diode laser absorption spectroscopy (TDLAS). In an exemplary embodiment, at least one chosen gas species partial pressure and fuel cell temperature within the fuel cell can be measured during fuel cell operation. In an exemplary system associated with the present disclosure, a fiber optic coupled diode light sensor is constructed and adapted to measure in-situ water vapor partial pressure within an active proton-exchange membrane (PEM) fuel cell.

An exemplary PEM fuel cell according to the present disclosure includes a bipolar plate adapted to allow for transmission of a near infrared laser beam through at least one flow channel on either a fuel or oxidizer side of the fuel cell's membrane-electrode assembly. A laser wavelength associated with the laser transmission is scanned over several water rotational and vibrational transitions occurring within the fuel cell. Light absorption is detected by measuring the transmitted laser power passing through the fuel cell system. Intensity and line shape of the measured transition is used to extract path-averaged values for particular gas species partial pressure.

In an exemplary embodiment, measurements are initially taken in a non-operating fuel cell. Using known temperature and humidity input gas streams associated with a base case non-operating system, calibration and testing of the optical device is achievable. The present disclosure further provides for exemplary techniques for rapid determination of water vapor partial pressure of an exemplary fuel cell. A particular optical technique associated with the present disclosure is applicable over a significant temperature and humidity operating range of a PEM fuel cell. The measurement technique can be applied to operating PEM fuel cell system(s) to examine the effects of incoming gas humidity and/or load on the gas partial pressure variation in at least one of a plurality of flow channels.

An exemplary system associated with the present disclosure is adapted to feeding partial pressure and/or temperature data into a controller of a fuel cell. The controller is adapted to (i) receive partial pressure and/or temperature data from one or more channels of a fuel cell; and (ii) incorporate the partial pressure and/or temperature data to optimize operating conditions. Exemplary operating conditions include but are not limited to: air flow rate, hydrogen flow rate, temperature, humidity (i.e., water flow rate), and/or load (i.e., voltage input). An exemplary controller can be adapted to receive multiple measurements in real-time thus allowing the overall fuel cell operation to be adjusted based on dynamic operating conditions. Examples of applicable systems capable of benefiting from the presently disclosed systems and/or methods include but are not limited to any vehicle or power source adapted to generating energy and/or power from a fuel cell, such as an automobile or a power generator.

An exemplary embodiment associated with the present disclosure generally provides for an optical technique for measuring at least one chosen gas species partial pressure and internal temperature within PEM fuel cells based on gas species absorption of light transmission through flow passages associated with a bipolar plate. A chosen gas species can include but is not limited to water vapor partial pressure, $CO$, $CO_2$, $CH_4$, $O_2$, $H_2$, and combinations thereof. Certain gas species are measurable depending on the wavelength of the light source used. In an exemplary embodiment, the chosen gas species partial pressure measured can be any gas species having a dipole moment adapted to absorb light transmission. In an exemplary embodiment, light is transmitted through at least one flow channel and transmission is measured by a light sensor. The measured light transmission is then compared to a transmission measurement of a reference light sensor. The difference in transmission values from reference to transmitted light represents absorption.

The present disclosure provides for an exemplary system adapted to permit non-intrusive in-situ measurements of partial pressure and temperature associated with operating conditions within a fuel cell. Non-intrusive in-situ measurements should enhance the capabilities of existing measurement techniques. Typically, an exemplary measurement approach associated with the present disclosure can be validated in steady-state operation of a PEM cell. Validation is typically accomplished by operating the cell under controlled humidity of incoming gas streams and cell temperature conditions.

When testing a PEM fuel cell for validation or studies, optical measurements can be applied to the PEM cell. Often, measurements are taken while the fuel cell is undergoing induced cyclic loading during the test. Typically, the loading is meant to simulate conditions that may be present in transportation applications where instantaneous power requirements fluctuate. An example of such an application includes but is not limited to an automobile. The measurements of gas partial pressure and temperature in a cathode flow passage of the bipolar plate generally detail the time response of an exemplary measuring system to transient events. Thus, an exemplary measuring system according to the present disclosure can be adapted to calibrate a fuel cell and/or input parameters to the fuel cell or fuel cell controller based on data received from the validation testing.

In an exemplary embodiment, a TDLAS system is adapted to alter the laser wavelength to access multiple water transitions with different temperature sensitivities. This can typically enable simultaneous recovery of both water vapor partial pressure and gas-phase temperature associated with fuel cell operation. The TDLAS system can be adapted to provide for sufficient temporal resolution to examine the variations in gas-phase composition and temperature in a single localized flow passage associated with a bipolar plate during unsteady-state fuel cell operation. An exemplary system is adapted to yield effective measurement results related to a fuel cell running under both steady and dynamic conditions including simulated non-uniform loading that might occur in practical applications.

The present disclosure provides for exemplary systems for measurement of fuel cell operating conditions using TDLAS. This is achieved by launching a laser beam into at least one narrow flow channel associated with a PEM fuel cell and detecting light absorption. In an exemplary embodiment, light absorption can be detected using a photodiode light sensor. In a further exemplary embodiment, unique signal analysis procedures are utilized to obtain both partial pressure and gas temperature in a single laser wavelength scan. This allows for measurements at high repetition rates, thus, allowing for a plurality of measurements over a relatively short time period. By utilizing a unique selection of laser wavelength, sensitivity of the temperature measurement can be significantly extended relative to existing TDLAS measurement systems.

Improved features over existing systems associated with present disclosure include but are not limited to: (1) ability to make temperature measurements in narrow flow channel(s) associated with PEM fuel cells non-intrusively and generally exhibiting high data acquisition rates; (2) data analysis procedures generally enabling extraction of both water vapor partial pressure and gas temperature simultaneously from one measurement; and/or (3) water transition selection for high sensitivity temperature measurements generally within the range of temperatures typically required for fuel cell applications.

An exemplary system associated with present disclosure includes a measuring system that can feed partial pressure and/or temperature data of a fuel cell into a controller of the fuel cell. In an exemplary embodiment, the controller is adapted to: (i) receive partial pressure and/or temperature data from one or more channels of a fuel cell; and (ii) incorporate the partial pressure data to optimize operating conditions such as air flow rate, hydrogen flow rate, temperature, humidity (i.e., water flow rate), and/or load (i.e., voltage input).

Unlike systems associated with existing measurement techniques that currently only receive partial pressure readings at an exhaust of the fuel cell and/or must take manual gas samplings for analysis, the present disclosure provides for systems that can be adapted to take multiple measurements in almost real-time, thus allowing the overall fuel cell operation to be adjusted based on dynamic operating conditions. Moreover, the present disclosure provides for an exemplary system capable of partial pressure and temperature measurements across different segments of the channel, not merely at the exhaust as currently limited by existing systems.

The present disclosure provides for an exemplary system utilizing TDLAS to measure a chosen gas species partial pressure and gas temperature. This is achieved through using wavelength selection that is appropriate for simultaneous determination of both parameters. Accordingly, in an exemplary embodiment, advantageous adjustments to the fuel cell operation can be made by spectral fitting of measured absorption profiles from which the partial pressure is determined from a half-width variation of absorption spectra. Moreover, temperature can be determined from peak absorption.

FIG. 1 illustrates an exemplary testing schematic for an exemplary measuring system 10 according to the present disclosure. In an exemplary embodiment, system 10 includes a bipolar fuel cell 100. Fuel cell 100 can be any power generating fuel cell including but not limited to a PEM fuel cell. Laser light source 14 (also referred to as Laser 14) transmits laser light through at least one flow channel 101 associated with fuel cell 100. In an exemplary embodiment, a photodiode light sensor (PD1) measures the incoming wavelength of the incoming laser transmission. Typically, an optical splitter 114 is utilized to allow for PD1 to receive an initial laser transmission measurement. PD1 can be referred to as a reference light sensor. PD1 provides for a reference measurement to later be compared to an absorption measurement generated through a second photodiode light sensor (PD2). PD2 is adapted to receive the output laser transmission after passing through flow channel 101.

Both PD1 and PD2 feed wavelength data back to a data acquisition and laser controller computer 11. Controller 11 is adapted to communicate with a laser source temperature controller 12 and a laser source current controller 13. Controllers 12 and 13 are adapted to adjust the laser transmission from laser 14 in response to a communication from controller 11. In an exemplary embodiment, controller 11 receives measurements from PD1 and PD2 and adjusts controllers 12 and 13 in response to the measurements. In an exemplary embodiment, controller 11 communicates appropriate parameter adjustments in controllers 12 and 13 to ensure fuel cell 100 is operating under desired conditions.

System 10 further includes at least two humidifiers, a hydrogen ($H_2$) humidifier 15 and an air humidifier 16. Hydrogen humidifier 15 receives an inlet hydrogen stream 17 to mix with a body of water 110. A mixture of water and hydrogen flows to the fuel cell from humidifier 15 via fuel cell $H_2$ inlet stream 17'. Fuel cell 100 receives inlet stream 17' via inlet 102. Air humidifier 16 receives an inlet air stream 118 to mix with body of water 111. A mixture of water and air flows to the fuel cell from humidifier 16 via fuel cell air inlet stream 18'. Fuel cell 100 receives stream 18' via inlet 103.

Flow rates associated with streams 17' and 18' can be adjusted through an $H_2$ flow valve 107 and an air flow valve 108 respectively. In an exemplary embodiment, flow valves 107 and 108 are in communication with a fuel cell controller computer 19. Controller 19 is adapted to adjust flow rates of flows 17' and 18' via valves 107 and 108 respectively. Controller 19 is further adapted to receive temperature measurements of the fuel cell from at least a first thermocouple TC1. Thermocouple TC1 is coupled to a heating source that is externally coupled to the fuel cell to effectuate temperature change of the fuel cell. Adjustments to valves 107 and 108 can be made in response to TC1 measurements. Each humidifier 15 and 16 includes a thermocouple TC2 and TC3 respectively. TC2 and TC3 allow for monitoring humidifier temperature to ensure effective operating conditions with respect to system 10.

In an exemplary embodiment, controller 19 is in communications with an electric load box 20 adapted to deliver voltage and/or increase load to fuel cell 100. Box 20 can be a Scribner Electric Load Box as illustrated in FIG. 1. Box 20 delivers load to fuel cell 100 to simulate potential dynamic operating conditions. This affords several testing benefits including but not limited to effective studying of fuel cell parameters under dynamic conditions, calibration of the fuel cell and fuel cell optimization.

Figure 2:
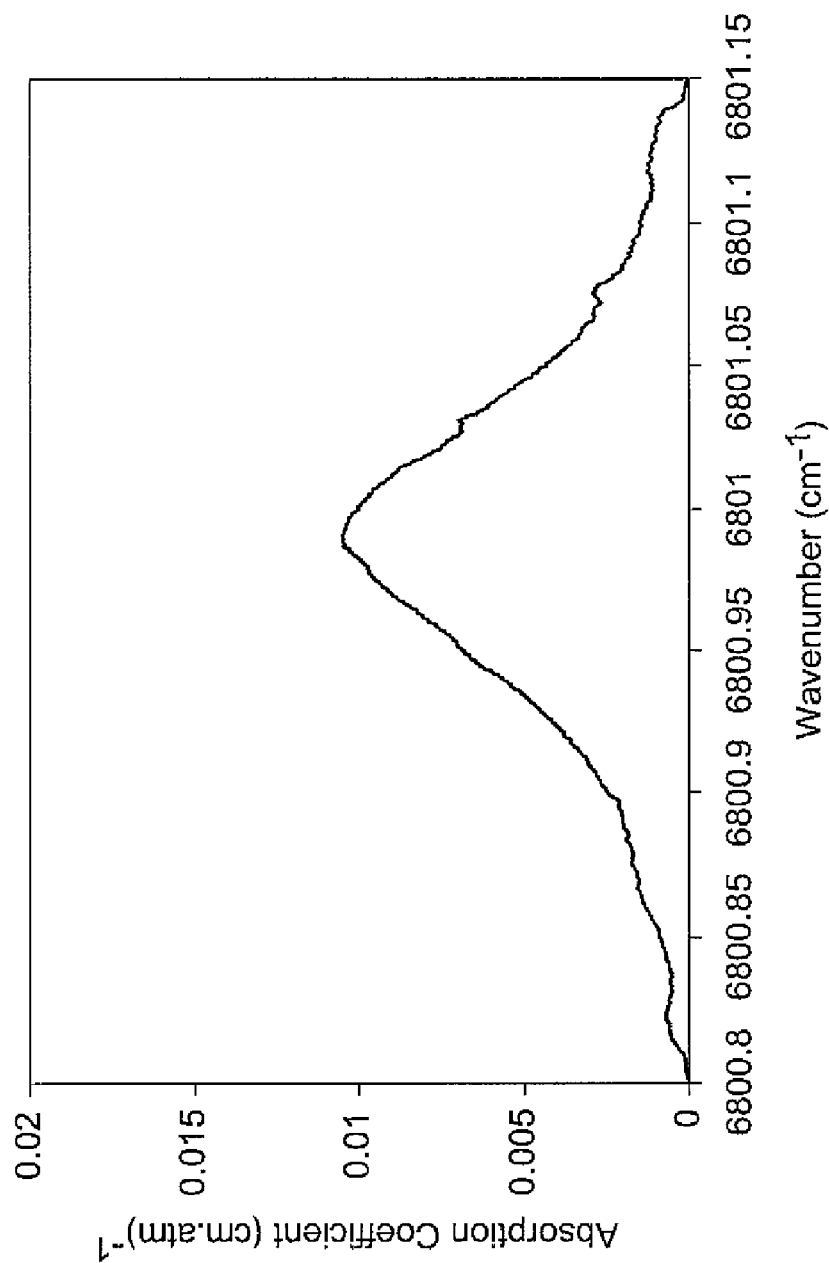
FIG. 2 is a graph illustrating exemplary sample spectrum measured in an exemplary fuel cell system according to the present disclosure using tunable diode laser absorption spectroscopy (TDLAS)
Figure 3:
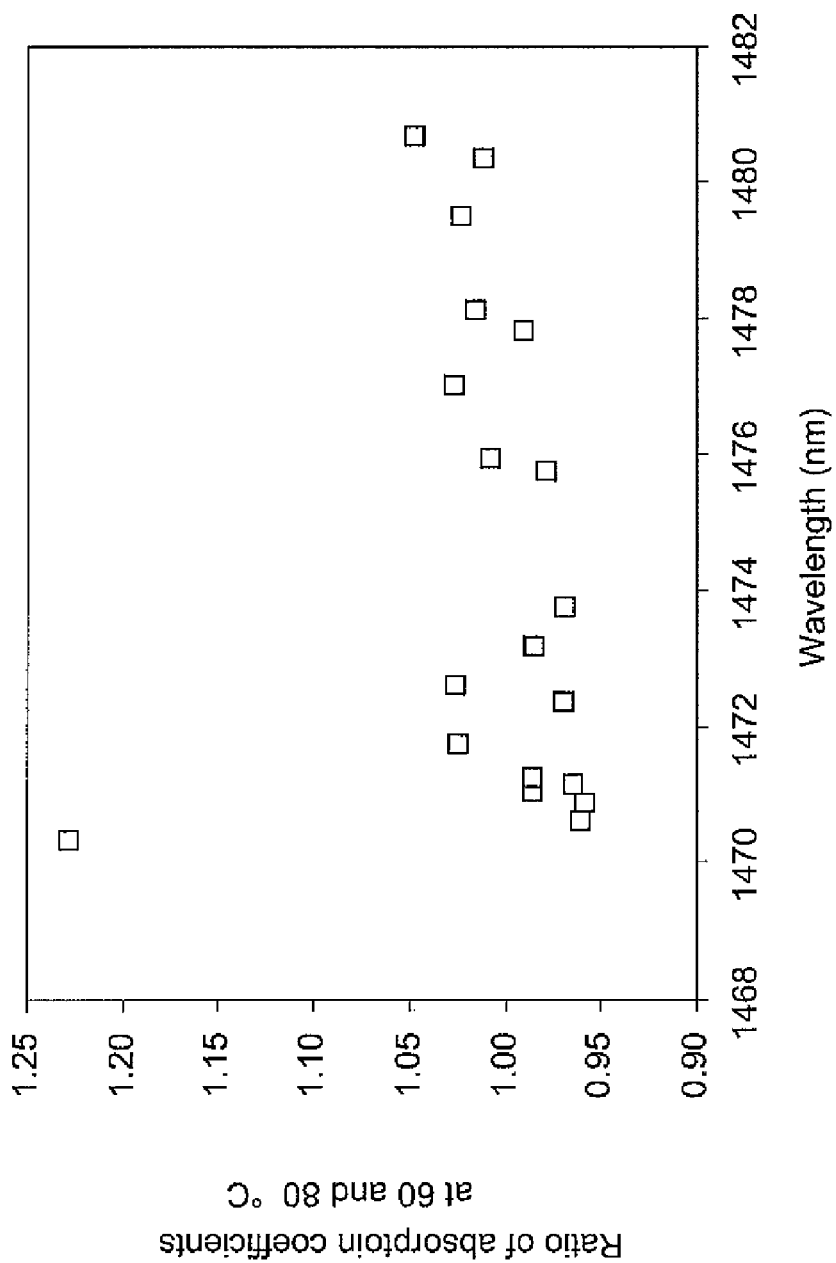
FIG. 3 is a graph illustrating ratio of absorption coefficients at about 60° C. and about 80° C. versus line center wavelength with respect to an exemplary testing of a system associated with the present disclosure.

Measurement calibration graphs for water vapor partial pressure and temperature parameters are represented in FIGS. 2 and 3 respectively. Several benefits can result through appropriate selection of spectral range as well as obtaining both temperature and water partial pressure data from a single scan associated with a selected spectral region. This allows calibrating parameters of an exemplary fuel cell to operate under desired conditions. Moreover, an operable laser wavelength with respect to a given fuel cell temperature, load, configuration and length conditions can also be determined.

In an exemplary embodiment, the present disclosure provides for a system adapted to measure liquid species concentration and fuel cell temperature in a single phase fuel cell application. Examples of single phase fuel cell applications include but are not limited to methanol or ethanol. With respect to a single phase embodiment, concentration of a chosen species such as methanol, ethanol, $CO_2$, $O_2$, CO, $H_2O$ and combinations thereof is measured using the technique(s) previously described with respect to gas phase applications.

To further illustrate applications and advantages associated with the present disclosure, reference is made to the following examples. However, it is to be understood that such examples are not limiting with respect to the scope of the present disclosure, but are merely illustrative of exemplary implementations and/or utilities thereof. The following examples describe exemplary systems and methods for simultaneous water vapor concentration and temperature measurements.

EXAMPLE 1

TDLAS is a particular technique effective in measuring water vapor absorption profiles as a function of excitation wavelength. However, the present disclosure describes systems and methods that differ from the prior art methodology in that, the operating temperature associated with the fuel cell is much lower than previously described temperature environments such as combustion vapor concentration measurements. Accordingly, different temperature ranges require unique laser wavelength regimes in order to accomplish effective measurements. In an exemplary embodiment, a laser and/or wavelength associated with the laser is selected to enable measurement of water transitions in a different wavelength regime.

The present disclosure provides for an exemplary system wherein a fiber pig-tailed output of a distributed feedback (DFB) diode laser (NEL # NLK1S5G1AA) at a wavelength of 1470 nm, for example, in a near-IR range is split by an optical splitter such as a 2×2 fiber splitter. Typically, a first leg of the splitter is adapted to be directly coupled to a sensor, such as a photodiode, serving as a reference measurement of the laser power without water absorption (Io). The output from a second leg is adapted to pass through an optically accessible PEM fuel cell using a modified bipolar plate.

The bipolar plate can typically be adapted to define a serpentine geometry such that long flow passages extend over the entire fuel cell width. In an exemplary embodiment, a bipolar plate includes a plurality of flow channels. In a further exemplary embodiment, a bipolar plate includes at least three channels. Each of the at least three channels can be identified as a first, a second and a third channel. In an exemplary embodiment, the third channel extends from an air inlet on a cathode side and is milled out to an opposite end of the bipolar plate. It is further fitted with two miniature collimating optics such that the laser emission can pass through the cell.

Although reference is being made to the third channel, the exemplary diagnostic technique described herein is equally as effective for all other channels associated with the fuel cell. Moreover, multiple channel monitoring is achievable through multiplexing. In an exemplary multi-channel embodiment, a plurality of sensors, such as photodiodes, are disposed to measure the flow channels of the fuel cell. Each sensor is adapted to measure laser transmission through at least one flow channel. Each photodiode is adapted to receive a laser transmission across the flow channel to measure laser absorption. In an exemplary embodiment, a multiplexing device is used to receive the plurality of sensor measurements and feeding the measurements to a laser controller.

In an exemplary embodiment, the total absorption path length is about 7 cm. Since the measurement technique associated with the present disclosure for determining water partial pressure is linear, the measurement recovers the path averaged value of partial pressure. In a linear path averaged value embodiment, variations of measured pressure characteristics (resulting from absorption data) along the line-of-sight cannot be determined. In prior art embodiments, flow passages were sealed with small windows at each end of the passage and the laser transmission was collimated externally. Alignment of these prior art systems is tedious since the length to width ratio of the channel is approximately 100 to 1. In the exemplary embodiment described herein, the bipolar plate(s) are configured by placing small collimating lenses, coupled with optical fibers, directly in each end of the flow passage(s). Each configuration is adapted to serve as both a seal to the flow passage and collimate the laser beam. The laser transmission passes through an alignment fiber optic which is coupled directly in the fuel cell improving the repeatability of laser alignment and forming a seal thereof.

Referring again to FIG. 1, in an exemplary embodiment according to the present disclosure, the laser output is captured using a similar photodiode (PD2) as the photodiode (PD1) used to measure the reference beam. The output photodiode (PD2) measures the attenuated laser power (I) passing through cell 100 including absorption from water and non-resonant losses. The hydrogen and other gas streams fed to fuel cell 100 are typically humidified by passing them through a temperature controlled (TC2 and TC3) water bath (110 and 111) to saturate the streams (17' and 18'), as shown in FIG. 1. Further heating of the gas streams (17' and 18') and heating the outer surface of the fuel cell provides independent control of gas and fuel cell temperatures and saturated stream humidity. In an exemplary embodiment, electrical heating pads 104 are coupled on the external fuel cell surface.

In an exemplary embodiment, external electrical load on fuel cell 100 is controlled by a fuel cell test system load box 20, such as a Scribner 890CL. For calibration of an exemplary system 10, cell 100 is fed with heated moist air of known relative humidity but is not fed with hydrogen. Alternatively, cell 100 is electrically loaded so that no electrochemical reaction occurs to alter the relative humidity of the cell. In an exemplary embodiment, dry to fully saturated conditions can be achieved for temperatures generally ranging from about 60 to 85° C., usually within the range of interest for PEM fuel cells. However, should fuel cells be designed to operate at different temperatures and/or conditions, system 10 can be calibrated to determine a suitable laser wavelength, thus adapted to be operable for any fuel cell design.

In an exemplary embodiment, the internal fuel cell pressure is atmospheric. The absorption of the laser beam passing through the gas sample is related to the partial pressure, $P_s$(atm), of the absorbing species according to Beer's law (see, e.g., S. S. Penner, *Quantitative Molecular Spectroscopy and Gas Emissivities*, pp. 1-15, Addison-Wesley, 1959):

$$\frac{I}{I_0} = \exp\left(-\int_0^L \kappa \cdot P_s \, dl\right) \quad (1)$$

According to Beer's law, $\kappa(\text{atm}^{-1}\text{cm}^{-1})$ is the wavelength and temperature dependent absorption coefficient. The mathematical integration is performed over the path length L of the gas sample through the bipolar plate. The absorption coefficient ($\kappa$) displays strong peaks as a function of wavelength due to the discrete rotational and vibrational energy transitions of molecular species. The absorption coefficient (K) is also temperature dependent resulting from the distribution of water molecules among its various energy levels. Also, the width of each transition depends on temperature.

Referring again to FIG. 1, a suitable DFB laser 14 can typically have a spectral bandwidth that is much narrower than the molecular transitions. The laser's wavelength depends on both the laser temperature and the current used to drive the diode laser. In an exemplary embodiment, an imbedded thermoelectric cooler (not shown) positioned within laser 14 and a laser source temperature controller 12 are each adapted to individually and/or cooperatively control the laser temperature and permit coarse tuning of the laser wavelength over its range. In an exemplary embodiment, the temperature is held constant during measurements.

In an exemplary embodiment, a current controller 13, such as a Thorlabs LDC5000, is adapted to generate rapid variation of laser wavelengths by altering the current injection into the diode laser 14. The laser current is adapted to be modulated with a 500 Hz ramp function generated with a data acquisition computer 11. This ramp modulation is adapted to alter the power as well as the wavelength of laser emission. In an exemplary embodiment, the laser wavelength can be varied over 0.15 nm and scanned through water absorption features. The reference photodiode (PD1) directly monitors the laser power prior to entering fuel cell 100 to account for its variation with injection current. In an exemplary embodiment, peak laser absorption is typically around 2%. Thus, the water absorption features appear as small dips in a measured laser intensity analysis emerging from the test cell. By taking the ratio of the laser intensity before and after the test cell ($I/I_0$), the relative absorption is determined as a function of time. An example of the measured absorption spectrum for an exemplary laser is shown in FIG. 2.

An optical spectrum analyzer (not shown) can be used to calibrate the laser wavelength as a function of temperature and current. Data from the photodiodes is typically acquired at rate of about 500 kHz collecting about 2000 samples for each current scan resulting in a scan time of about two milliseconds. In an exemplary embodiment, 500 scans are averaged to obtain absorption data, which are in turn processed to determine other parameters such as water vapor partial pressure and temperature.

Spectral Simulations:

Ro-vibrational transitions available at 1491 nm are typically not sufficiently sensitive to temperatures in the range from about 60° C. to 90° C. The absorption intensity varies by only about 10% and the spectral width varies by only about 2.2%. Moreover, difficulties develop when extracting temperature in addition to water partial pressure under such environments. An exhaustive analysis was performed with respect to water spectrum from about 1400 nm to about 1650 nm. This was carried out to determine transitions that are suitable for temperature measurements generally within the range of interest with respect to PEM cells. The range of about 1400-1650 nm was selected since commercially available, relatively inexpensive diode lasers are manufactured in this range. It is understood, however, the present disclosure is adaptable to any range made available in the future.

Under typical fuel cell operation, hot spots can develop causing pinholes or burns in the membrane, thus negatively effecting fuel cell operation and performance. The present disclosure provides for exemplary systems and methods that allow for simultaneous partial pressure and temperature measurements such that, inter alia, hot spots resulting from fuel cell operation within the fuel cell can be monitored before pinholes begin developing in the membrane. In an exemplary embodiment, measuring temperature facilitates control of operational parameters. This may prevent negative effects with respect to the fuel cell and thus improving performance.

In an exemplary embodiment, a simulation of water absorption spectra using an HITRAN database (see, e.g., L. S. Rothman, C. P. Rinsland, A. Goldman, S. T. Massie, E. D. P. Edwards, J. M. Flaud, A. Perrin, C. Camy-Peyret, V. Dana, J. Y. Mandin, J. Schroeder, A. McCann, R. R. Gamache, R. B. Wattson, K. Yoshino, K. V. Chance, K. W. Jucks, L. R. Brown, V. Nemtchinov, P. Varanasi, *J. Quant. Spectrosc. Radiat. Trans.*, 60 (1998) 665-710), was executed over a range of about 1400-1650 nm at typical PEM conditions of water partial pressure of about 0.19 atm and temperatures of about 60° C.-80° C. The ro-vibrational transitions of water vapor were simulated using a Voigt function convolution with the HITRAN intensity and width data. It was found in previous experiments that absorption coefficients greater than 0.0035 $(cm \cdot atm)^{-1}$ could be accurately measured with direct absorption in the PEM cell. Thus, an intensity cut-off was introduced to filter out spectral lines with absorption coefficients below 0.0035 $(cm \cdot atm)^{-1}$. The purpose was to extract absorption coefficients, which are accurately measurable, and to ascertain their temperature sensitivity.

The simulated absorption coefficients at temperatures of about 60° C. and about 80° C. were divided by one another to determine the relative change in absorption with temperature only at fixed partial pressure. FIG. 3 illustrates these results for all transitions meeting the threshold absorptivity requirement at wavelengths between about 1468 and 1482 nm (a subset of the entire range examined). The transition near 1470 nm shows a 23% variation of peak absorption coefficient with temperature, which is the greatest temperature sensitivity of all lines examined. All the other transitions in the wavelength range of about 1400-1650 nm have temperature sensitivities much less than 20%. The NEL laser (NLK1S5G1AA) was thus selected for measurements in this region.

Figure 4:
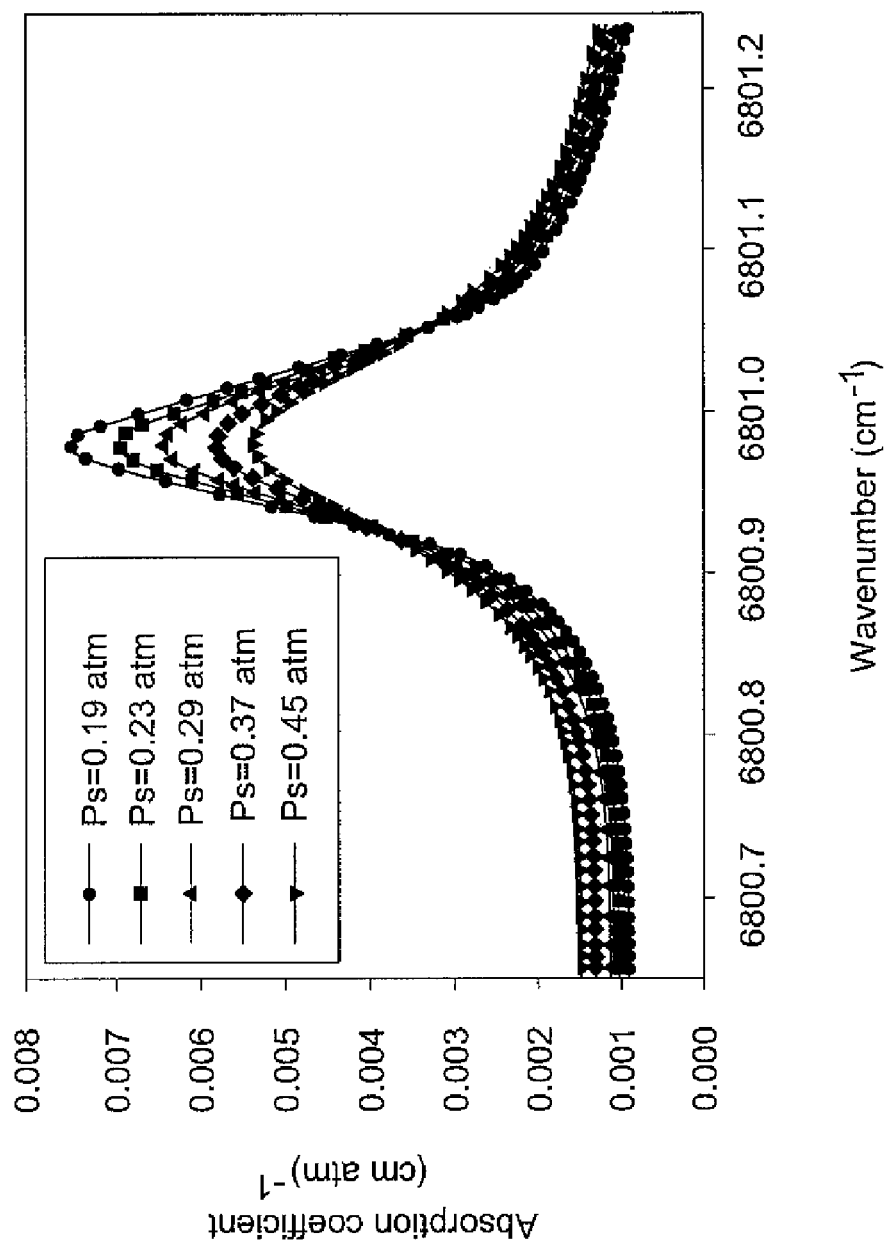
FIG. 4 is a graph illustrating simulated absorption profiles for different partial pressures at T=80° C. associated with testing of an exemplary fuel cell system according to the present disclosure.

An exemplary methodology for extracting partial pressure and temperature simultaneously was developed based on the HITRAN simulations. FIG. 4 illustrates the simulated absorption profiles in the range of about 1470.30-1470.42 nm (6800.75-6801.3 $cm^{-1}$) across the temperature sensitive water feature for a fixed temperature of about 80° C. with respect to different water partial pressures. Water-water collisions are very effective at broadening water absorption profiles (compared to water-air collisions). Thus, the width of the profile changes substantially with water partial pressure. Moreover, the increase in profile width is so strong that the peak intensity of the water absorption decreases with increasing water partial pressure. Since the temperature remains constant, this half-width change is dominated by the Lorentzian part of the Voigt profile, which governs collisional broadening. Consistent with previous analysis, a Lorentzian profile can be used in place of the more complicated Voigt profile to describe the profile shape with minimal error. For this exemplary transition, the width varies by about 60% for water partial pressure variations of about 0.19-0.45 atm.

Figure 5:
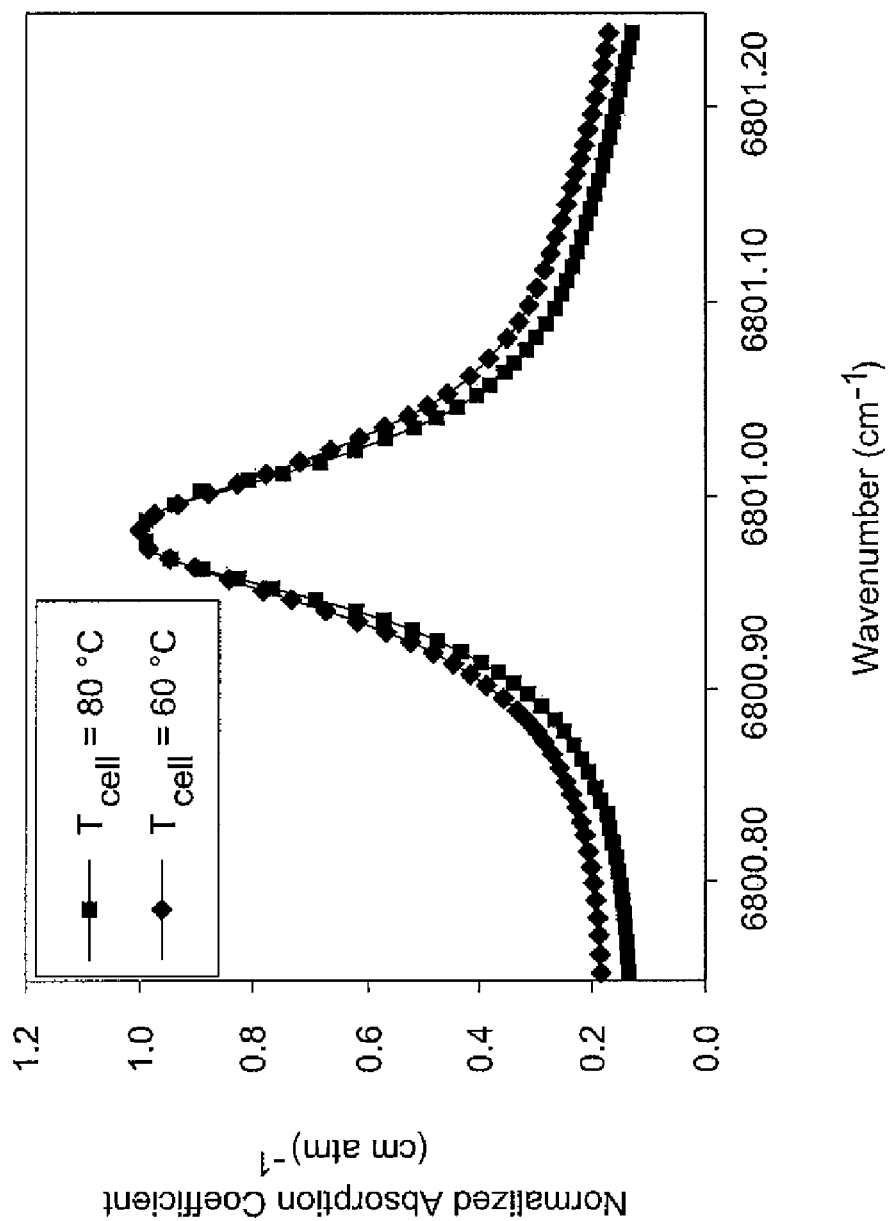
FIG. 5 is a graph illustrating normalized absorption profiles at about 60° C. and about 80° C. for $P_s$=0.19 atm associated with testing of an exemplary fuel cell system according to the present disclosure.

FIG. 5 illustrates simulated normalized water spectra for cold and hot conditions often expected in a PEM fuel cell at a partial pressure of about 0.19 atm. Absorption peaks vary by about 23% for a change of temperature of about 20° C. However, less than about 5% change in the profile width is observed, which is dominated by collisional broadening of water-water collisions as is evident from FIG. 5. Thus, width and intensity of measured profiles can be effective to extract simultaneously water partial pressure and temperature data. This was not possible in the prior art references since the laser wavelength available probed a temperature insensitive water transition.

Figure 6:
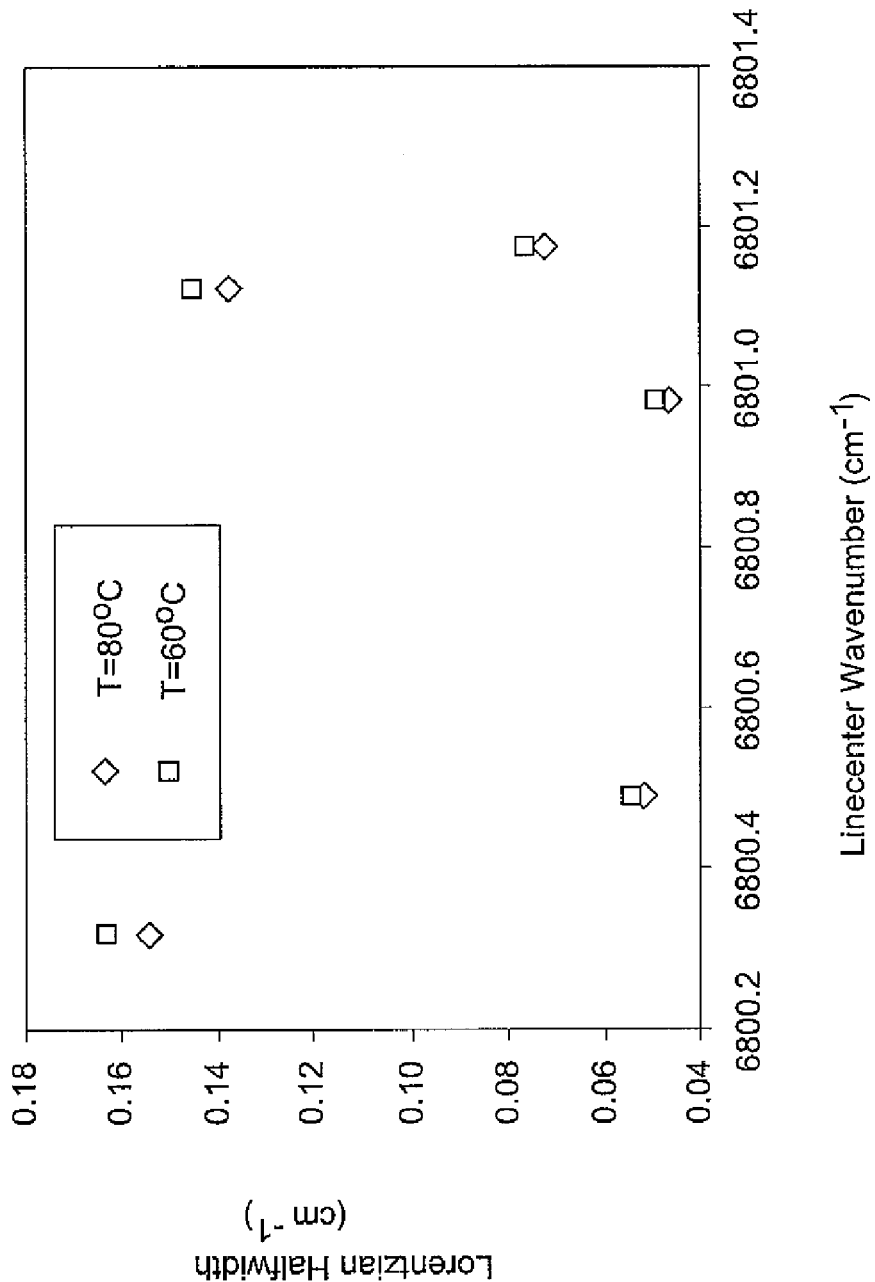
FIG. 6 is a graph illustrating variation of Lorentzian half-width with temperature associated with testing of an exemplary fuel cell system according to the present disclosure.
Figure 7:
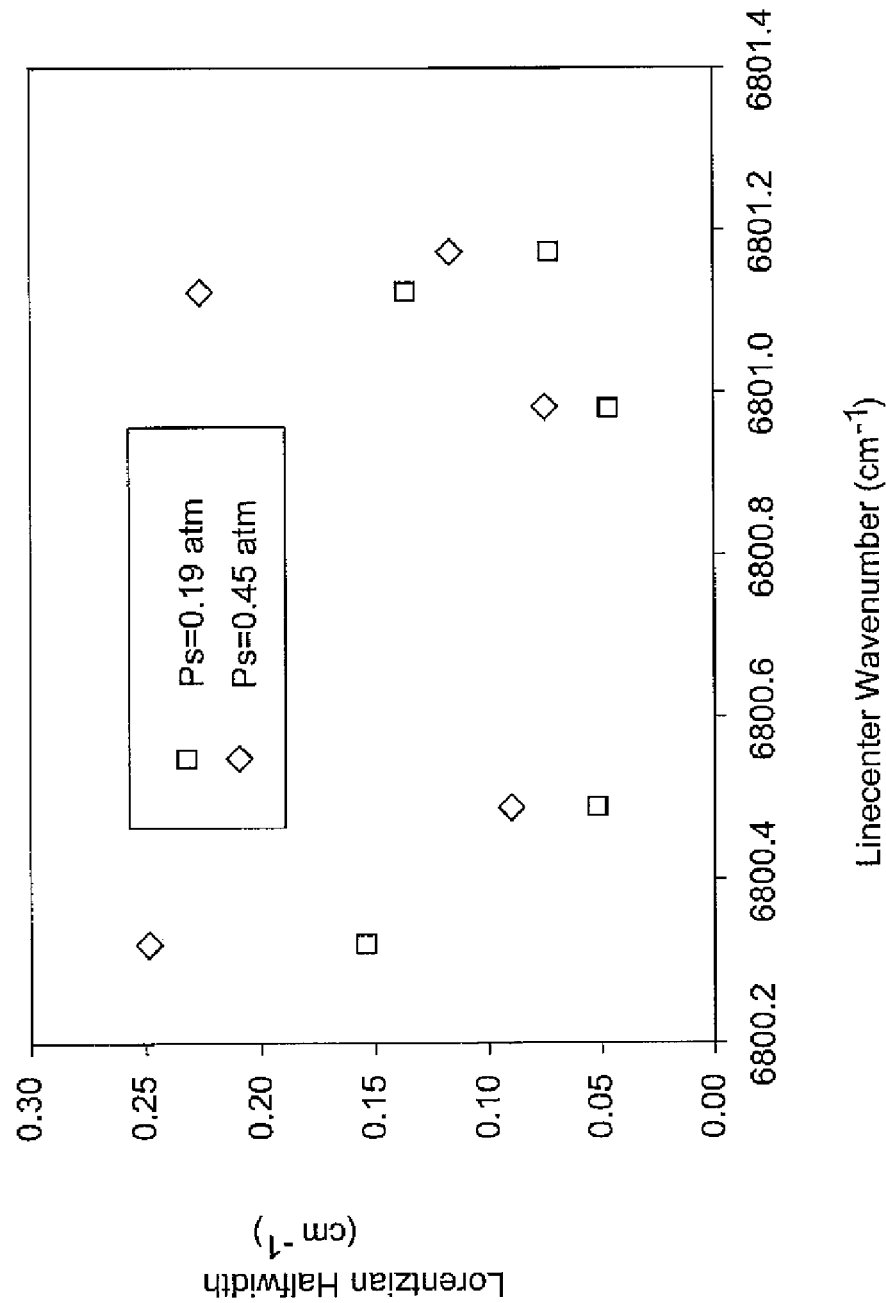
FIG. 7 is a graph illustrating variation of Lorentzian half-width with partial pressure at T=80° C. associated with testing of an exemplary fuel cell system according to the present disclosure.

FIGS. 6 and 7 illustrate certain advantageous features associated with the present disclosure. Predicted profile half-widths are shown for five separate transitions, each adapted to be accessible with an NEL laser acquired for these measurements. The variation with temperature (FIG. 6) is very small in each case, while the variation with partial pressure (FIG. 7) is significant. Thus, a curve fit to the measured data is effective to extract the partial pressure independent of temperature from the half-width. Since the peak intensity is both a function of partial pressure and temperature, knowledge of the partial pressure can then be used to extract the temperature from the peak intensity.

Figure 8:
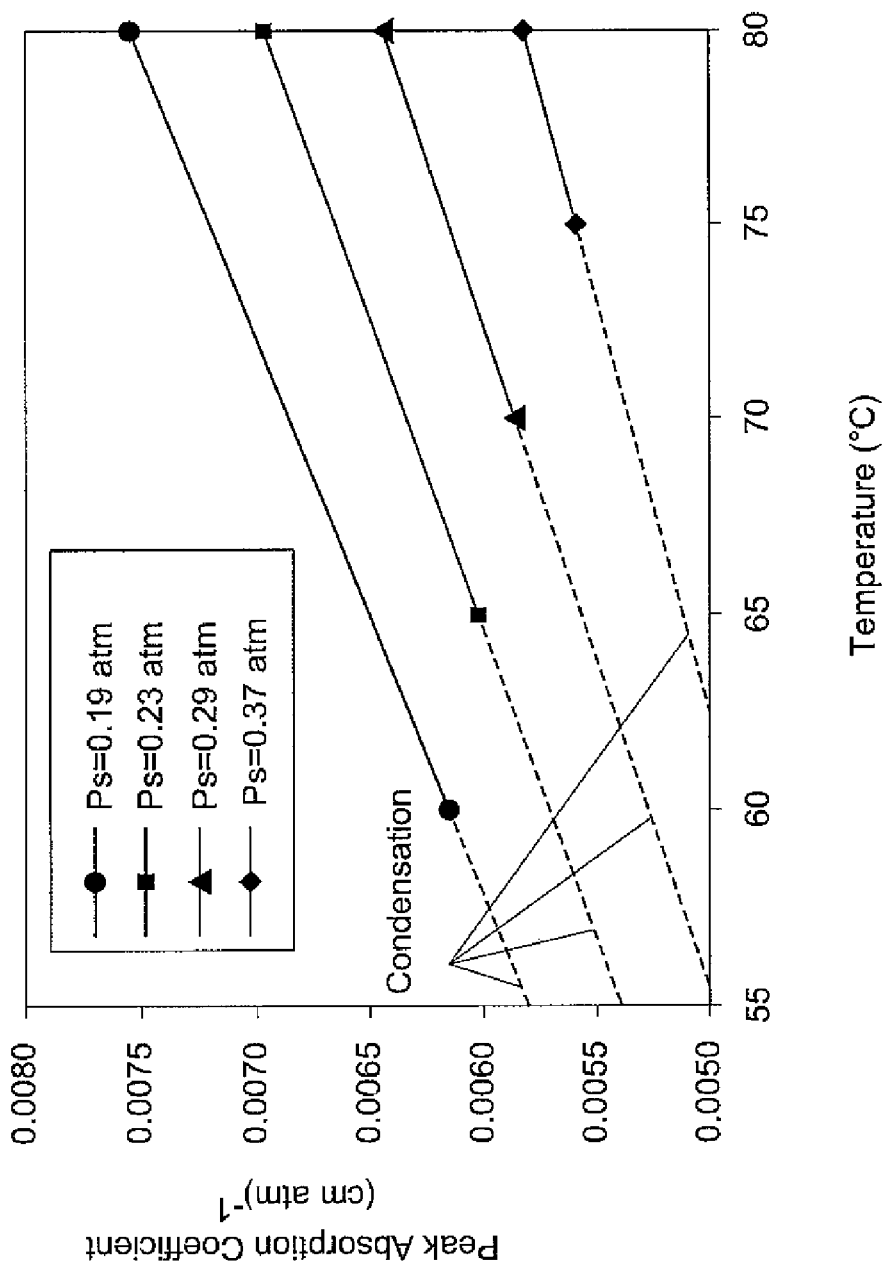
FIG. 8 is a graph illustrating variation of peak absorption coefficients with temperature for different partial pressure conditions associated with testing of an exemplary fuel cell system according to the present disclosure.

FIG. 8 illustrates variation of peak absorption coefficient with respect to temperature for various partial pressure conditions based on HITRAN simulations. Once the partial pressure is obtained from a half width, a constant partial pressure line is chosen and the peak absorption coefficient is related to the temperature. The dashed lines indicate a zone where water becomes saturated at a predicted temperature so that two-phase flow would exist in the bipolar plate. No data in this zone is possible since condensation inside the gas channels prevent transmission of the laser beam. Moreover, the loss of absorption signal is a good indicator of water condensation in the flow channel as a result of beam path blockage. The spacing between the iso-partial-pressure lines is sufficient for an accurate determination of both temperature and water vapor partial pressure as demonstrated in the exemplary measurements described herein. Since these measurements are based on equilibration of rotational molecular energy modes, which are much faster than the dynamic processes occurring in fuel cells, this technique is applicable for steady-state and dynamic operation of the fuel cell.

EXAMPLE 2

System Calibration

In an exemplary embodiment, measurements are first made in a fuel cell without external loading or hydrogen flow. This allows for calibrating measured half-widths and spectral intensities against simulated data profiles. As established from the previously described HITRAN simulation, the exemplary profiles are typically Lorentzian. In the spectral window available with an exemplary laser, about five water transitions typically contribute significantly to the overall absorption shape. Data analysis procedure consists of fitting five Lorentzian profile shapes over generated data, similar to previous curve fittings associated with a different spectral range (see, e.g., B. H. Armstrong, *J. Quant. Spectrosc. Radiat. Trans.*, 7, (1966) 61-68).

Figure 9:
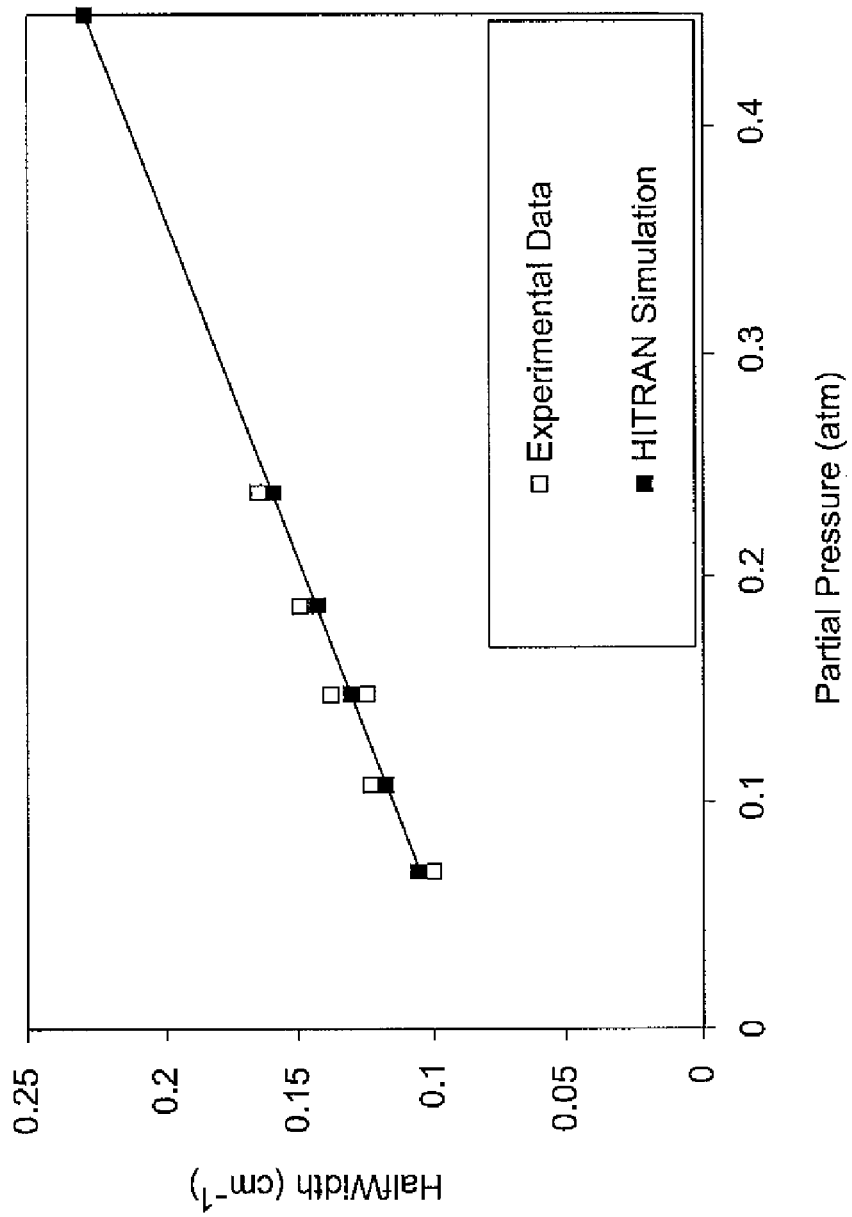
FIG. 9 is a graph illustrating half-width calibration versus partial pressure associated with testing of an exemplary fuel cell system according to the present disclosure.
Figure 10:
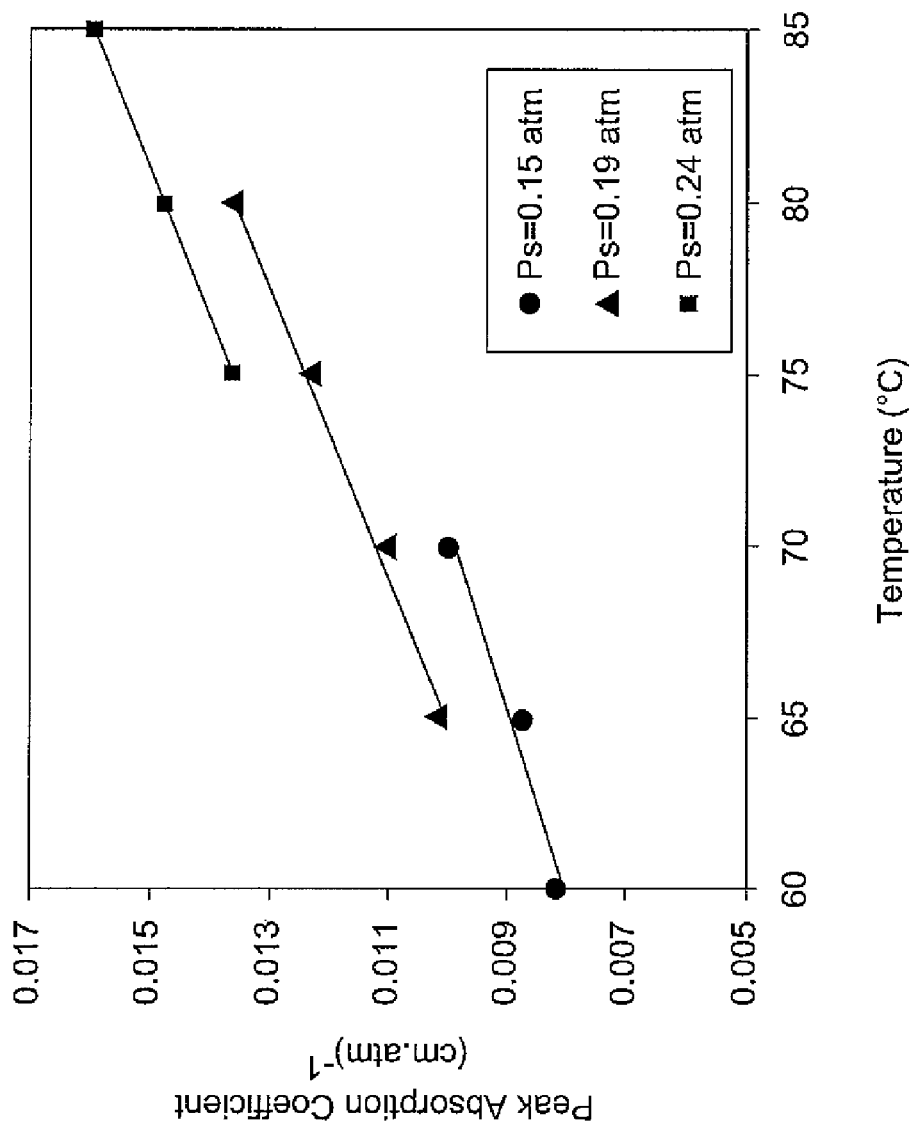
FIG. 10 is a graph illustrating calibration of peak intensities versus temperature associated with testing of an exemplary fuel cell system according to the present disclosure.

Line central wavelengths of the five Lorentzians are taken from the HITRAN database and widths and peak intensities of about five Lorentzians are varied. In addition, a third order polynomial curve fit to a slowly varying background is included. The half-width and intensity of a preferred transition of interest at about 6801 cm$^{-1}$ can be used for further analysis. FIG. 9 graphically illustrates measured and simulated profile half-widths for this line versus partial pressure. In the calibration examples, the temperature and partial pressure are known since they are externally controlled. Good agreement results between theoretical half-width versus partial pressure and an exemplary counterpart within about 10% over a wide range of partial pressure values. FIG. 10 shows measured peak intensities as a function of water partial pressure and temperature, both controlled with respect to the calibration analysis.

Peak intensity is related to temperature linearly and separate calibration lines for each partial pressure result as predicted in FIG. 8. Shift in peak intensity at a fixed temperature with variation of partial pressure is due to line broadening as shown in FIG. 4. This calibration diagram is subsequently used in active fuel cell measurements to determine temperature once partial pressure of water is determined from measurements associated with FIG. 9.

EXAMPLE 3

Steady-State Fuel Cell Tests

In an exemplary embodiment, measurements of water partial pressure and temperature are carried out on an air (cathode) side of an exemplary fuel cell. Operating temperature of the fuel cell is varied over a range from about 60° C. to 80° C. Relative humidity of air and H$_2$ flow streams entering cathode and anode sides of the fuel cell are also varied from about 40 to 90%. In an exemplary embodiment, air flow rate is maintained at about 1.2 lpm while that of hydrogen is fixed at about 1.0 lpm for the measurement techniques disclosed herein. External load is varied as a step function so that each load setting corresponds to a particular value of current density drawn from the cell.

Figure 11A:
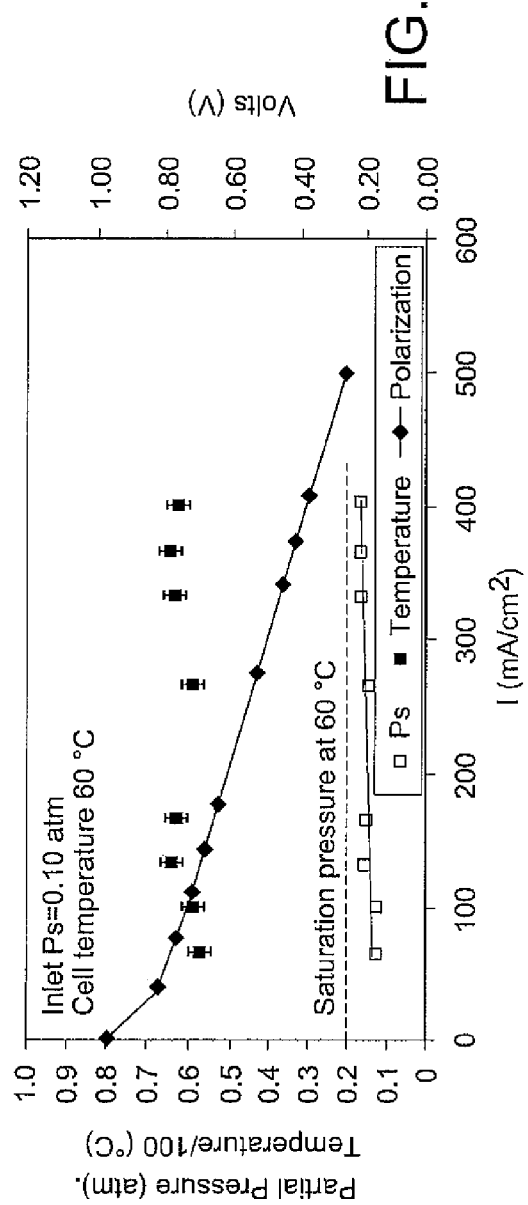
FIGS. 11(a) and (b) are graphs illustrating partial pressure and temperature measurements under steady-state operation at (a) 60° C. ($P_{sat}$=0.20 atm) and (b) 75° C. ($P_{sat}$=0.38 atm) associated with testing of an exemplary fuel cell system according to the present disclosure.
Figure 11B:
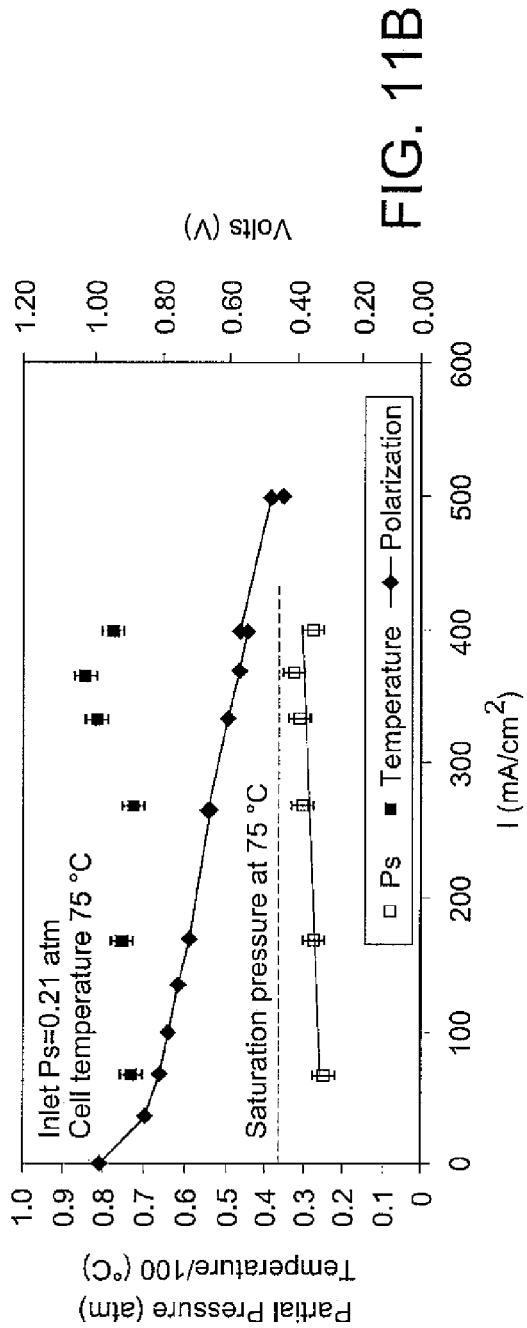

Spectroscopic measurements are carried out at each value of the load after allowing the cell to reach steady-state operation. FIG. 11(a-b) illustrate water partial pressures and temperatures measured and/or equated under these conditions using calibration curves associated with FIGS. 9 and 10. Water vapor partial pressure rises from an inlet value as more current is drawn from the cell. As load on the fuel cell increases, the current and therefore proton flux also increases. Increased current produces more water at the cathode side and results in increased water partial pressure observed. Since temperature of the cell is controlled by an external heating pad and is allowed to reach steady-state for each operating condition, steady-state temperature profiles do not show significant changes as current is increased with respect to low currents. At higher currents, heat production in the cell is large enough to show a 5-10° C. rise in the local gas-phase temperature.

An error estimate associated with the results can be determined from the calibration curve for partial pressure in FIG. 9, where the scatter of the data points about the linear fit is about ±5%, similar to measurements associated with using a different laser system. Error in temperature measurement may arise from three sources: (1) measurement noise seen as scatter of data points about a linear best fit of FIG. 10; (2) error from linear interpolation of temperature if the value of peak intensity falls in between two calibrated pressure lines; and (3) the ±5% uncertainty associated with measurement of partial pressure, which in turn results in an uncertainty in locating an iso-partial pressure line for temperature determination. All these sources of error combined results in an uncertainty of ±2.5° C. in temperature determination from measured data.

EXAMPLE 4

Fuel Cell Tests Under Simulated Dynamic Conditions

Figure 12:
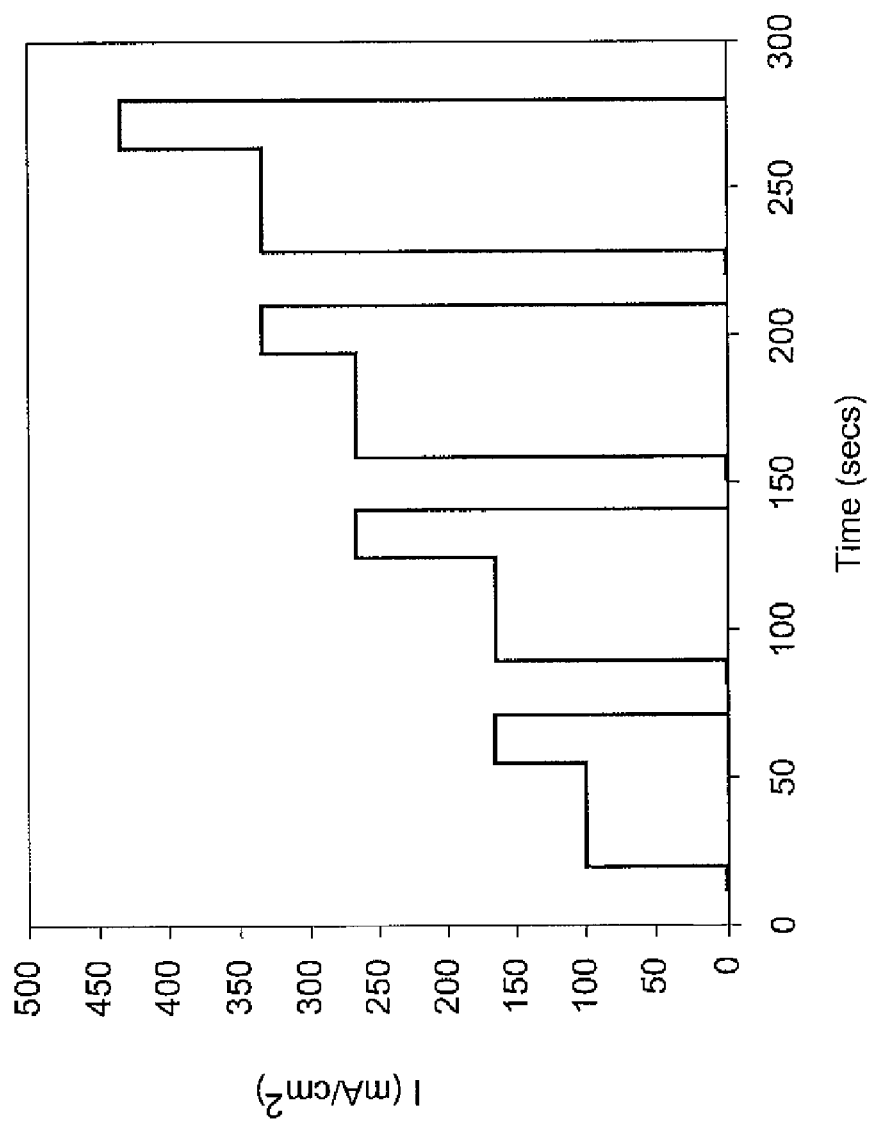
FIG. 12 is a graph illustrating a sample dynamic cycle associated with operation of an exemplary fuel cell system according to the present disclosure.

In addition to temperature recovery, a particular advantageous aspect associated with the present disclosure includes extension of measurements of fuel cell gas-phase properties to fuel cells undergoing dynamic cycling. Dynamic condition testing is of importance, particularly with respect to the automobile industry. Procedures associated with previously described calibration profile generation is generally applicable with respect to dynamic condition testing with the exception of at least one exemplary embodiment. External load on an exemplary fuel cell is varied according to a load schedule recommended by the U.S. Fuel Cell Council (see, e.g., *US Fuel Cell Council, Protocol on Fuel Cell Component Testing*, www.usfcc.com). A particular external load sequence, shown in FIG. 12, has a total cycle time of about 300 seconds.

Figure 13:
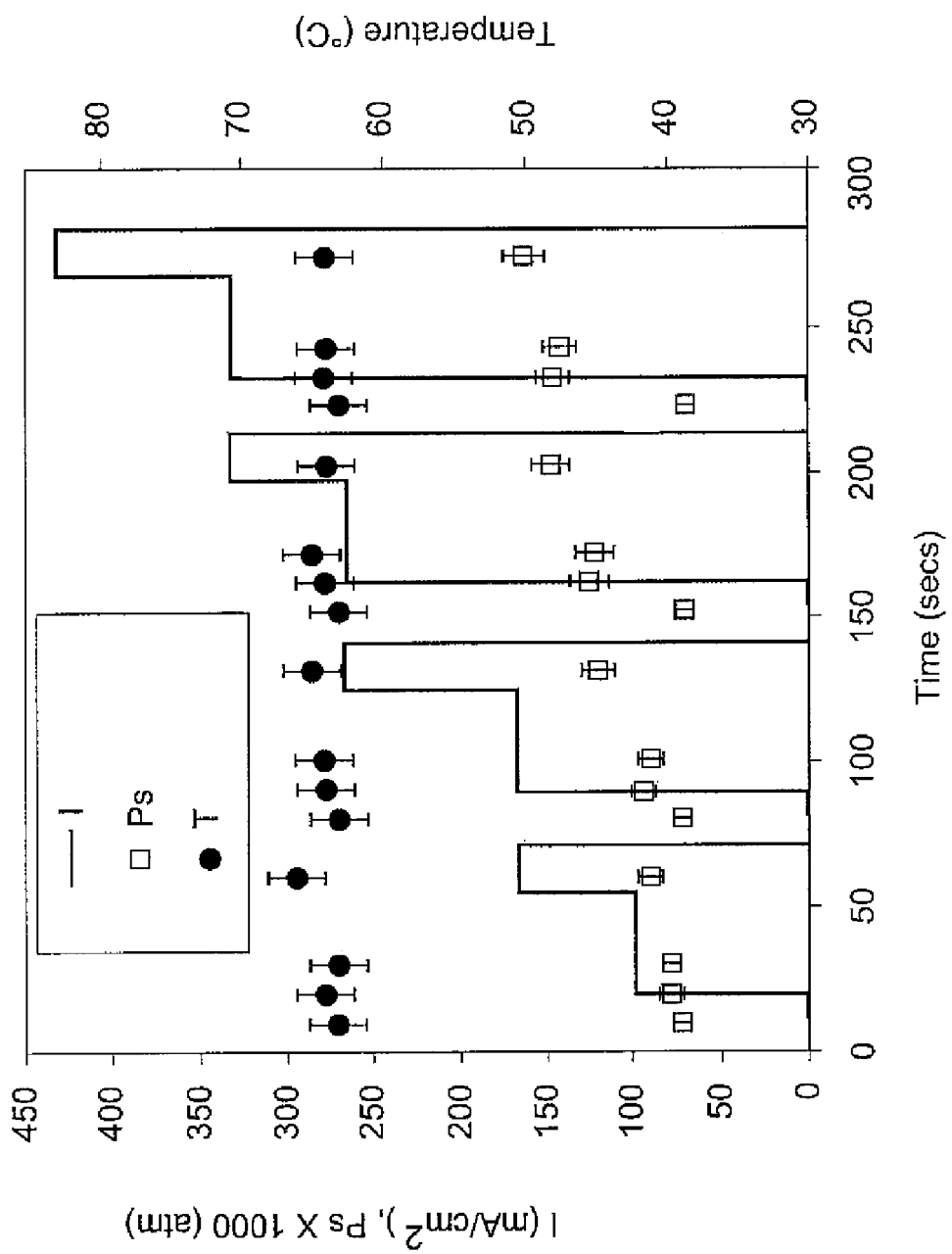
FIG. 13 is a graph illustrating partial pressure and temperature measurements for inlet $P_s$=0.07 atm, cell temperature=60° C. ($P_{sat}$=0.20 atm) with dynamic cycling associated with operation of an exemplary fuel cell system according to the present disclosure.

In an exemplary embodiment, measurements of water absorption spectra and resulting partial pressures and temperatures are taken just before, during rise, and near end of each dynamic feature in a particular load cycle. FIG. 13 illustrates partial pressure and temperature profiles for a fuel cell operating under a dynamic cycle with nominal cell temperature at about 60° C. and inlet water vapor partial pressure in the air stream of about 0.07 atm.

With respect to these exemplary operating conditions, cell temperature does not significantly vary. However, water partial pressure is observed to increase during each dynamic load feature as more current is drawn. Water partial pressures measured immediately after the fast rise in each feature are identical to those measured 10 seconds later. This indicates that gas composition follows electrical loading very rapidly. Likewise, after each load is removed rapidly, water partial pressure returns to inlet value within 10 seconds. These measurements show that the time response of the cell is significantly less than 10 seconds to follow these rapid changes.

Figure 14:
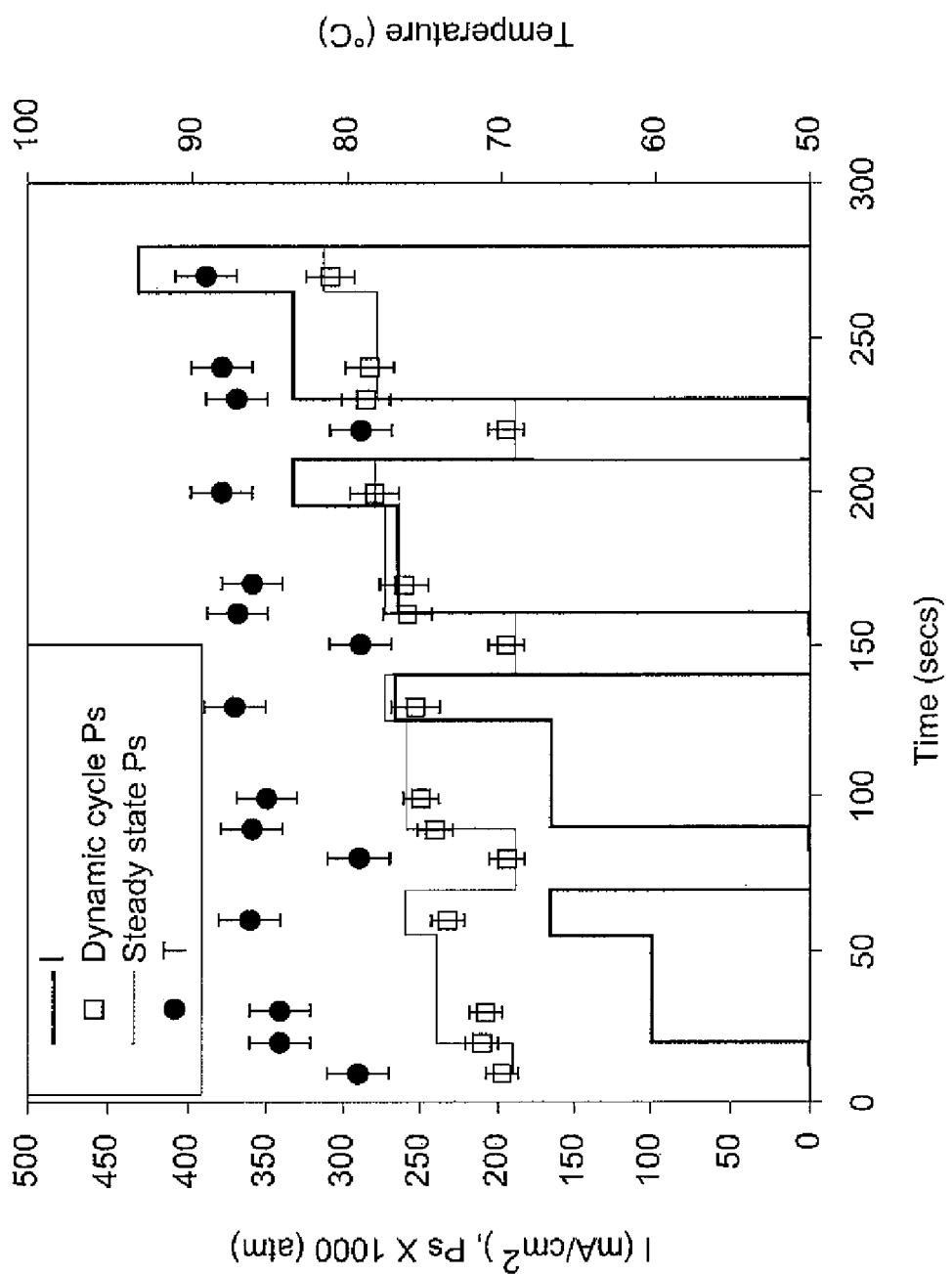
FIG. 14 is a graph illustrating partial pressure and temperature measurements for inlet $P_s$=0.19 atm, cell temperature=80° C. ($P_{sat}$=0.47 atm) with dynamic cycling associated with operation of an exemplary fuel cell system according to the present disclosure.

FIG. 14 illustrates similar measurements during similar load cycles but with a nominal cell temperature of about 80° C. and an inlet water partial pressure of about 0.19 atm. A dashed line in FIG. 14 represents values of water partial pressure that would be obtained under steady-state conditions under similar cell temperature and current, based on measurements associated with FIGS. 11(a-b). Quasi-steady-state values are slightly higher than values measured under dynamic cycling for low currents. During the last half of the dynamic load cycle, when the peak current is higher, the actual and quasi-steady values are equal. Thus, the fuel cell reaches a value closer to quasi-steady conditions when cycling to higher currents.

As with measurements associated with a colder cell, measurements made about 10 seconds after a fast fall feature in a cycle have attained inlet partial pressure values. Thus, for both previously described operating conditions, the time response of the gas-phase properties are less than about 10 seconds. Moreover, the time response should be much less than 10 seconds to achieve complete equilibration when the cell is unloaded. It should be noted that the measurements referred to with respect to the previously described exemplary embodiments are spatially averaged across a channel length with a temporal resolution of about 8 seconds; thus, local and temporal variations from these results with finer resolution cannot be excluded.

With respect to relatively hotter fuel cell operating conditions, cell temperature noticeably rises during each load cycle feature, as shown in FIG. 14. While the cell is nominally controlled at about 80° C., the local temperature in the gas passage of the bipolar plate typically rises as high as about 90° C. due to the rapid cycling of the cell from the steady-state value. The external temperature control cannot follow these rapid changes. The temperature is controlled by a temperature controller whose response time and time needed for heat to dissipate and make the cell attain the nominal value is large compared to the cell cycling time. Partial pressure on the contrary is not controlled by external means. For partial pressure, it is chemical kinetics responsible for adjusting to the dynamic cycling associated with external load. FIG. 14 suggests that the chemical kinetics and water transport is fast enough to reach nearly quasi-steady-state conditions.

In an exemplary embodiment, the present disclosure relates to measurement of partial pressure and temperature during both steady-state and dynamic cycle operation of a PEM fuel cell. Diagnostic techniques associated with the present disclosure are adapted to monitor laser transmission and water absorption through at least one flow passage associated with a bipolar plate. Simulations of water absorptivity are utilized to select a laser wavelength that optimizes sensitivity to temperature and partial pressure for operating conditions associated with a PEM fuel cell. Calibration measurements in a non-operating cell are used to validate exemplary operating parameter models. A laser system according to the present disclosure is effective to facilitate measurements in a steady-state cell, and is adapted to further extend to include temperature measurements and measurements of both temperature and water partial pressure during dynamic fuel cell operation. Dynamic operating conditions can be simulated to represent environments that may occur in applications such as automotive, where power demand fluctuates.

Non-intrusive in-situ measurements do not disturb fuel cell operation. Moreover, experimental data indicates that gas-phase properties follow external loading with a time response of less than about 10 seconds. However, the internal temperature in flow passages associated with the bipolar plate is not fully regulated by external fuel cell heating pads and it shows a significant, about 10° C., increase during dynamic fuel cell operation.

Systems and methods associated with present disclosure offer significantly enhanced techniques for measuring gas partial pressure and temperature of a fuel cell in-situ. Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

What is claimed:

1. A system for measuring partial pressure and temperature within a fuel cell, comprising:
   (a) a fuel cell having a proton exchange membrane (PEM)-electrode assembly and a bipolar plate, the bipolar plate including at least one flow channel to allow for transmission of light through the at least one flow channel;
   (b) at least one light source to transmit light through the at least one flow channel;
   (c) at least one reference light sensor for measuring the light transmitted from the light source prior to passing through the at least one flow channel; and
   (d) at least one transmission light sensor for measuring the light transmitted through the at least one flow channel; wherein the measured light transmitted through the at least one flow channel represents light absorption through the flow channel and is processed along with the reference light measurement to determine values for at least one of a gas species partial pressure or a fuel cell temperature.

2. The system according to claim 1, wherein the at least one flow channel associated with the bipolar plate includes oppositely positioned first and second collimating lenses coupled with optical fibers, and wherein each collimating lens is positioned at opposite ends of the flow channel.

3. The system according to claim 2, wherein the optical fibers are selected with reference to a specific wavelength associated with the light source and with reference to an absorption profile of a gas species.

4. The system according to claim 1, wherein the light source is a laser light source and the transmitted light is a laser beam.

5. The system according to claim 4, wherein the bipolar plate includes at least one flow channel to allow for transmission of a near infrared laser beam through the flow channel.

6. The system according to claim 1, wherein the gas species is a gas selected from the group consisting of water vapor, CO, CO2, CH4, H2, O2, and combinations thereof.

7. The system according to claim 1, wherein the measured light transmission is characterized by tunable diode laser absorption spectroscopy (TDLAS).

8. The system according to claim 1, wherein the light measurements are taken during steady-state fuel cell operation.

9. The system according to claim 1, wherein the light measurements are taken during dynamic fuel cell operation.

10. The system according to claim 1, wherein the reference light sensor and the transmission light sensor are photodiode sensors characterized by a fiber optic coupled diode-sensor.

11. The system according to claim 1, wherein the transmitted light is characterized by a light wavelength transmitted over several water rotational and vibrational transition states in the fuel cell.

12. The system according to claim 1, wherein the bipolar plate includes a plurality of flow channels, and wherein each of the plurality of flow channels allows for light to pass through the flow channel and be measured by a light sensor.

13. The system according to claim 1, wherein light measurements are taken in a non-operating fuel cell having input gas streams of known humidity allowing for calibration of fuel cell parameters.

14. The system according to claim 13, wherein the parameters are selected from the group consisting of light absorption, gas inputs to the fuel cell, operating temperature, humidity of gas inputs and combinations thereof.

15. The system according to claim 1, wherein light measurements are taken in a non-operating fuel cell having input gas streams of known humidity allowing for testing of fuel cell response to different fuel cell parameters.

16. The system according to claim 1, wherein the light measurements are taken during fuel cell operation to allow for examining effects of incoming gas humidity and load on water vapor partial pressure in the at least one flow channel.

17. The system according to claim 1, wherein the partial pressure and temperature values resulting from measured light transmission are received by at least one fuel cell controller to process the measured light values and, based on the measurements, control output of at least one system component selected from the group consisting of a heating source to heat the fuel cell, at least one humidifier to humidify at least one inlet stream into the fuel cell, a load box or external circuit to apply load on the fuel cell, and combinations thereof to operate the fuel cell at desired operating conditions.

18. The system according to claim 1, wherein the partial pressure values resulting from measured light transmission and the reference light transmission sensor are received by at least one data acquisition and laser controller to process the measured values and based on the measurements control output of at least one system component selected from the group consisting of a light source temperature controller, a light source current controller and combinations thereof to transmit light at a desired wavelength.

19. The system according to claim 1, wherein several measurements are taken across the at least one flow channel to generate at least one parameter profile for at least one known parameter versus the partial pressure and temperature measurements.

20. The system according to claim 2, wherein the collimating lenses: (i) seal the flow channel; and (ii) collimate the transmitted light.

* * * * *